United States Patent [19]

Aoyagi et al.

[11] Patent Number: 5,952,202
[45] Date of Patent: Sep. 14, 1999

[54] METHODS USING EXOGENOUS, INTERNAL CONTROLS AND ANALOGUE BLOCKS DURING NUCLEIC ACID AMPLIFICATION

[75] Inventors: Kazuko Aoyagi, Emeryville; Kenneth J. Livak, San Jose, both of Calif.

[73] Assignee: The Perkin Elmer Corporation, Foster City, Calif.

[21] Appl. No.: 09/048,880

[22] Filed: Mar. 26, 1998

[51] Int. Cl.[6] .............................. C12P 19/34; C12Q 1/68; C07H 21/04

[52] U.S. Cl. ........................... 435/91.2; 435/6; 435/91.1; 536/24.31; 536/24.32; 536/24.33

[58] Field of Search ............................. 435/6, 91.1, 91.2; 536/24.31, 24.32, 24.33

[56] References Cited

U.S. PATENT DOCUMENTS

| | | | |
|---|---|---|---|
| 5,538,848 | 7/1996 | Livak et al. | 435/91.2 |
| 5,763,186 | 6/1998 | Ludtke et al. | 435/6 |

OTHER PUBLICATIONS

Walker et al (NAR vol. 22, No. 13 pp. 2670–2677, 1993.
PE Applied Biosystems Taqman Internal Positive Control, 1998.
Andrus, Alex, "Chemical methods for 5'non–isotropic labelling of PCR probes and promers, "*PCR 2: A Practical Approach*Oxford Iniversity Press, Osford, pp. 39–54 (1995).
Beaucage et al., "Advances in the Synthesis of Oligonucleotides by the Phosphoramadite Approach," *Tetrahedron 48 (12)*:2223–2311 (1992).
Cardullo et al., Detection sof nucleic acid hybridizatin by nonradiative florescence resonance energy transfer, *Proc. Natl. Acad. Sci. USA*85:8790–8794 (Dec. 1988).
Egholm et al., "PNA hybridizes to complememtary oligonucleotides obeying the Watson–Crick hydrogen–bonding rules," *Nature 365*566–568 (Oct. 1993).
Gilliland et al., Analysis of cytokine mRNA and DNA: Detection and quantitation by competitive polymerase chain reaction, *Proc. NAtl. Acad. Sci. USA*87:2725–2729 (Apr. 1990).
Hermanson, Greg T., *Bioconjugate TEchniques,* Academic Press, San Diego, Californai, pp. 40–55 (1996).
Higushi et al., "Simulataneous Amplification and Detection of Specific DNA Sequences," *Biotechnology* 10:413–417 (April, 1992).

(List continued on next page.)

*Primary Examiner*—Kenneth R. Horlick
*Assistant Examiner*—Jeffrey Siew
*Attorney, Agent, or Firm*—Scott R. Bortner

[57] ABSTRACT

Reporter-quencher probe assays of nucleic acid amplification, such as PCR, are rendered more meaningful by the addition of internal control reagents. An internal control polynucleotide is amplified with internal control primers and the product is measured by correlation with increased fluorescence by polymerase mediated-exonuclease cleavage or hybridization of the internal control probe. Probes specific for target and internal control polynucleotides are labelled with spectrally resolvable reporters, allowing for concurrent detection and measurement of target and control amplification. A kit of all PCR reagents can be dispensed into reaction chambers in a high-throughput system for rapid and accurate nucleic acid amplification assay, with real-time or end-point measurements. Fluorescent signals correlated to target and internal control levels are spectrally resolvable and measured concurrently. A non-extending oligonucleotide or nucleic analog "block", complementary to the internal control polynucleotide, is added to the amplification mixture to preclude amplification of the internal control polynucleotide and function as an internal negative control. The amplification control reagents, kits, and methods of the present invention provide positive and negative control tests occurring within, and measurable within, the reaction chamber.

18 Claims, 11 Drawing Sheets

OTHER PUBLICATIONS

Higuchi et al., "Kinetic PCR Analysis: Real–time Monitoring of DNA Amplification Reactions," *Bio/Technology* 10:413–417 (Apr. 1992).

Holland et al., "Detection of specific polymearse chain reaction product by utilizing the 5'→3'exonuclease activity of Thermus aquaticus DNA polymearse," *Proc. Natl. Acad. Sci. USA 88* :7276–7280 (Aug. 1991).

Kricka, Larry O., *Nonisotopic DNA Probe Techniques* Academic Press, San Diego, pp. pp. 3–28 (1992).

Lee et al., "Allelic discrimination by nick–translation PCR with fluorogenic probes," *Nucleic Acids Res.* 21(16):3761–3766 (1993).

Livak et al., "Oligonucleotides with Fluorescent Dyes at Opposite Ends Provide a Quenched Porbe System Useful for Detecting PCR Product and Nucleic Acid Hybridization," *PCR methods and Applications* 4:357–362 (1995).

Mullah et al., "Automated Synthesis of Double Dye–Labeled Oligonucleotides using Tetramethyrhodamine (TAMRA) Solid Supports," *Tetrahedron Letters 38(33)* 5751–5754 (1997).

Mullah et al., "Efficient synthesis of double Recognition of DNA by Strand Displacement with a Thymine–Substituted Polyamide," *Science* 254:1497–1500 (DEc. 1991).

Neilsen et al., "Sequence–Selective Recognition of DNA by Strand Displacement with Thymine–Substituted Polyamide," *Science* 254:1497–1500 (Dec. 1991).

Orum et al., "Single base pair mutation analysis by PNA directed PCR clamping," *Nucleic Acids. Res.* 21(23):5332–5336 (1993).

Perseptive Biosystems, "Identifying Point Mutations by PNA–Directed PCR Clamping,"1(1):1–4 (1995).

Tsai et al., "Quantification of mRNA using Competitve RT–PCR with Standard–Curve Methodlogy," *Biotechniques* 21(5):862–866 (Nov. 1996).

Tyagi et al., "Molecular Beacons: Probes that Fluoresece upon Hybridization," *Nature Biotechnology* 14:303–308 (Mar. 1996).

van der Laan et al., "A Covenient Automated Solid–Phase Synthesis of PNA–(5') –DNA–(3')–PNA Chimera," *Tetrahedron Letters* 38(13):2249–2252 (1997).

Vinayak et al., "Automoted Chemical Synthesis of PNA and PNA–DNA Chimera on a Nucleic Acid Synthesizer," *Nucleosides & Nucleotides 16 (7–9)* :1653–1656 (197).

Wang et al., "Quantitation of mRNA by the polymearse chain reaction," *Proc. Natl. Acad. Sci. USA* 86:9717–9721 (Dec. 1989).

Zimmermann et al., "Quantitative Multiple Competitive PCR of HIC–1 DNA in a Sinlge Reaction Tube," *Biotechniques 21(3)* :480–484 (Sep. 1996).

FAM

TET

HEX

JOE

| Dye | Emission maxima (nm) | Absorbance maxima (nm) |
|---|---|---|
| 5-FAM | 522 | 494 |
| 6-FAM | 518 | 492 |
| JOE | 554 | 528 |
| HEX | 553 | 535 |
| TET | 538 | 521 |
| TAMRA | 582 | 560 |
| ROX | 607 | 587 |

Figure 5.

96 Well, microtitre plate:

|   | 1    | 2    | 3    | 4    | 5    | 6    | 7    | 8    | 9    | 10   | 11   | 12   |
|---|------|------|------|------|------|------|------|------|------|------|------|------|
| A | IPC- | IPC- | IPC- | IPC- | IPC- | IPC- | IPC+ | IPC+ | IPC+ | IPC+ | IPC+ | IPC+ |
| B | IPC+ | IPC+ | IPC+ | IPC+ | IPC+ | IPC+ | IPC+ | IPC+ | IPC+ | IPC+ | IPC+ | IPC+ |
| C | IPC+ | IPC+ | IPC+ | IPC+ | IPC+ | IPC+ | IPC+ | IPC+ | IPC+ | IPC+ | IPC+ | IPC+ |
| D | IPC+ | IPC+ | IPC+ | IPC+ | IPC+ | IPC+ | IPC+ | IPC+ | IPC+ | IPC+ | IPC+ | IPC+ |
| E | IPC+ | IPC+ | IPC+ | IPC+ | IPC+ | IPC+ | IPC+ | IPC+ | IPC+ | IPC+ | IPC+ | IPC+ |
| F | IPC+ | IPC+ | IPC+ | IPC+ | IPC+ | IPC+ | IPC+ | IPC+ | IPC+ | IPC+ | IPC+ | IPC+ |
| G | IPC+ | IPC+ | IPC+ | IPC+ | IPC+ | IPC+ | IPC+ | IPC+ | IPC+ | IPC+ | IPC+ | IPC+ |
| H | IPC+ | IPC+ | IPC+ | IPC+ | IPC+ | IPC+ | IPC+ | IPC+ | IPC+ | IPC+ | IPC+ | IPC+ |

Sample assignment:

| wells  | reagents     | function                  | sample signal | IPC signal |
|--------|--------------|---------------------------|---------------|------------|
| A1-A6  | IPC, block   | no amplification control  | -             | -          |
| A7-A12 | IPC          | no template control       | -             | +          |
| B1-H12 | targets, IPC | unknowns, samples         | + or -        | +          |

Figure 7

| Well | Type | Sample | PCR | target ΔRn | target Ct |
|---|---|---|---|---|---|
| A1 | NAC | | No amp | 0.06 | 40 |
| A2 | NAC | | No amp | 0.06 | 40 |
| A3 | NAC | | No amp | 0.06 | 40 |
| A4 | NAC | | No amp | 0.06 | 40 |
| A5 | NAC | | No amp | 0.06 | 40 |
| A6 | NAC | | No amp | 0.06 | 40 |
| A7 | NTC | | - | 0.05 | 40 |
| A8 | NTC | | - | 0.05 | 40 |
| A9 | NTC | | - | 0.06 | 40 |
| A10 | NTC | | - | 0.04 | 40 |
| A11 | NTC | | - | 0.06 | 40 |
| A12 | NTC | | - | 0.05 | 40 |
| B1 | Unknown | 10,000 | + | 1.72 | 26.38 |
| B2 | Unknown | 1000 | + | 1.45 | 29.57 |
| B3 | Unknown | 100 | + | 0.81 | 33.04 |
| B4 | Unknown | 10 | + | 0.12 | 38.01 |
| B5 | Unknown | 1 | + | 0.14 | 37.94 |
| B6 | Unknown | 0.1 | - | 0.05 | 40 |
| B7 | Unknown | Negative | - | 0.05 | 40 |
| B8 | Unknown | Negative | - | 0.05 | 40 |
| B9 | Unknown | Negative | - | 0.05 | 40 |
| B10 | Unknown | Negative | - | 0.04 | 40 |
| B11 | Unknown | Negative | - | 0.05 | 40 |
| B12 | Unknown | Negative | - | 0.05 | 40 |
| C1 | Unknown | Negative | - | 0.05 | 40 |
| C2 | Unknown | Negative | - | 0.04 | 40 |
| C3 | Unknown | Negative | - | 0.04 | 40 |
| C4 | Unknown | Negative | - | 0.03 | 40 |
| C5 | Unknown | Negative | - | 0.04 | 40 |
| C6 | Unknown | Negative | - | 0.04 | 40 |
| C7 | Unknown | Negative | - | 0.04 | 40 |
| C8 | Unknown | Negative | - | 0.04 | 40 |
| C9 | Unknown | Negative | - | 0.04 | 40 |
| C10 | Unknown | Negative | - | 0.04 | 40 |
| C11 | Unknown | Negative | - | 0.05 | 40 |
| C12 | Unknown | Negative | - | 0.04 | 40 |
| D1 | Unknown | 10,000 | + | 1.66 | 26.25 |
| D2 | Unknown | 1000 | + | 1.35 | 30.17 |
| D3 | Unknown | 100 | + | 0.72 | 33.09 |
| D4 | Unknown | 10 | + | 0.28 | 36.09 |
| D5 | Unknown | 1 | - | 0.05 | 40 |
| D6 | Unknown | 0.1 | - | 0.04 | 40 |
| D7 | Unknown | Negative | - | 0.04 | 40 |
| D8 | Unknown | Negative | - | 0.04 | 40 |
| D9 | Unknown | Negative | - | 0.04 | 40 |
| D10 | Unknown | Negative | - | 0.04 | 40 |
| D11 | Unknown | Negative | - | 0.05 | 40 |
| D12 | Unknown | Negative | - | 0.05 | 40 |
| E1 | Unknown | Negative | - | 0.05 | 40 |
| E2 | Unknown | Negative | - | 0.04 | 40 |
| E3 | Unknown | Negative | - | 0.04 | 40 |
| E4 | Unknown | Negative | - | 0.05 | 40 |

FIG. 8A

| | | | | | |
|---|---|---|---|---|---|
| E5 | Unknown | Negative | - | 0.04 | 40 |
| E6 | Unknown | Negative | - | 0.05 | 40 |
| E7 | Unknown | Negative | - | 0.05 | 40 |
| E8 | Unknown | Negative | - | 0.05 | 40 |
| E9 | Unknown | Negative | - | 0.05 | 40 |
| E10 | Unknown | Negative | - | 0.05 | 40 |
| E11 | Unknown | Negative | - | 0.05 | 40 |
| E12 | Unknown | negative | - | 0.05 | 40 |
| F1 | Unknown | 10,000 | + | 1.65 | 40 |
| F2 | Unknown | 1000 | + | 1.37 | 40 |
| F3 | Unknown | 100 | + | 0.72 | 40 |
| F4 | Unknown | 10 | + | 0.67 | 40 |
| F5 | Unknown | 1 | - | 0.05 | 40 |
| F6 | Unknown | 0.1 | - | 0.04 | 40 |
| F7 | Unknown | negative | - | 0.05 | 40 |
| F8 | Unknown | negative | - | 0.05 | 40 |
| F9 | Unknown | negative | - | 0.05 | 40 |
| F10 | Unknown | negative | - | 0.05 | 40 |
| F11 | Unknown | negative | - | 0.05 | 40 |
| F12 | Unknown | negative | - | 0.04 | 40 |
| G1 | Unknown | negative | - | 0.05 | 40 |
| G2 | Unknown | negative | - | 0.04 | 40 |
| G3 | Unknown | negative | - | 0.06 | 40 |
| G4 | Unknown | negative | - | 0.05 | 40 |
| G5 | Unknown | negative | - | 0.04 | 40 |
| G6 | Unknown | negative | - | 0.04 | 40 |
| G7 | Unknown | negative | - | 0.05 | 40 |
| G8 | Unknown | negative | - | 0.04 | 40 |
| G9 | Unknown | negative | - | 0.05 | 40 |
| G10 | Unknown | negative | - | 0.05 | 40 |
| G11 | Unknown | negative | - | 0.05 | 40 |
| G12 | Unknown | negative | - | 0.04 | 40 |
| H1 | Unknown | negative | - | 0.05 | 40 |
| H2 | Unknown | negative | - | 0.04 | 40 |
| H3 | Unknown | negative | - | 0.05 | 40 |
| H4 | Unknown | negative | - | 0.04 | 40 |
| H5 | Unknown | negative | - | 0.04 | 40 |
| H6 | Unknown | negative | - | 0.04 | 40 |
| H7 | Unknown | negative | - | 0.04 | 40 |
| H8 | Unknown | negative | - | 0.05 | 40 |
| H9 | Unknown | negative | - | 0.04 | 40 |
| H10 | Unknown | negative | - | 0.04 | 40 |
| H11 | Unknown | negative | - | 0.04 | 40 |
| H12 | Unknown | negative | - | 0.04 | 40 |

FIG. 8B

| Well | Type | target ΔRn | Target Ct | ICP ΔRn | ICP Ct |
|---|---|---|---|---|---|
| A1 | NAC | 0.005 | 40 | 0.009 | 40 |
| A2 | NAC | 0.0007 | 40 | 0.01 | 40 |
| A3 | NAC | 0.01 | 40 | 0.001 | 40 |
| A4 | NAC | 0.002 | 40 | 0.01 | 40 |
| A5 | NAC | 0.003 | 40 | 0.002 | 40 |
| A6 | NAC | 0.005 | 40 | 0.0005 | 40 |
| A7 | NTC | 0.02 | 31.88 | 0.51 | 24.89 |
| A8 | NTC | 0.04 | 32.71 | 0.52 | 25.02 |
| A9 | NTC | 0.02 | 35.72 | 0.52 | 24.41 |
| A10 | NTC | 0.03 | 30.96 | 0.53 | 25.02 |
| A11 | NTC | 0.03 | 30.47 | 0.52 | 24.61 |
| A12 | NTC | 0.04 | 31.12 | 0.52 | 25.04 |
| B1 | Unknown | 1.41 | 17.1 | 0.54 | 24.35 |
| B2 | Unknown | 1.43 | 17.13 | 0.56 | 23.15 |
| B3 | Unknown | 1.43 | 16.93 | 0.52 | 25.65 |
| B4 | Unknown | 1.36 | 16.87 | 0.52 | 24.05 |
| B5 | Unknown | 1.40 | 17.18 | 0.51 | 25.45 |
| B6 | Unknown | 1.41 | 16.93 | 0.50 | 23.75 |
| B7 | Unknown | 1.43 | 16.87 | 0.52 | 26.41 |
| B8 | Unknown | 1.43 | 17.18 | 0.51 | 23.47 |
| B9 | Unknown | 1.36 | 16.83 | 0.55 | 25.03 |
| B10 | Unknown | 1.40 | 16.95 | 0.51 | 23.28 |
| B11 | Unknown | 1.41 | 17.20 | 0.54 | 25.91 |
| B12 | Unknown | 1.46 | 16.97 | 0.50 | 22.65 |
| C1 | Unknown | 1.41 | 16.73 | 0.53 | 25.03 |
| C2 | Unknown | 1.41 | 17.02 | 0.54 | 24.64 |
| C3 | Unknown | 1.39 | 20.79 | 0.51 | 24.52 |
| C4 | Unknown | 1.44 | 20.91 | 0.52 | 23.40 |
| C5 | Unknown | 1.35 | 21.17 | 0.54 | 24.98 |
| C6 | Unknown | 1.26 | 21.02 | 0.54 | 24.35 |
| C7 | Unknown | 1.25 | 20.88 | 0.53 | 24.92 |
| C8 | Unknown | 1.26 | 21.15 | 0.53 | 24.88 |
| C9 | Unknown | 1.20 | 21.00 | 0.52 | 25.01 |
| C10 | Unknown | 1.28 | 21.19 | 0.51 | 24.72 |
| C11 | Unknown | 1.24 | 21.01 | 0.51 | 24.64 |
| C12 | Unknown | 1.25 | 21.05 | 0.50 | 25.01 |
| D1 | Unknown | 1.26 | 21.07 | 0.53 | 24.58 |
| D2 | Unknown | 1.20 | 20.79 | 0.51 | 25.16 |
| D3 | Unknown | 1.26 | 21.05 | 0.51 | 24.97 |
| D4 | Unknown | 1.20 | 21.07 | 0.49 | 24.94 |
| D5 | Unknown | 0.98 | 25.33 | 0.53 | 24.87 |
| D6 | Unknown | 1.22 | 21.32 | 0.51 | 24.99 |
| D7 | Unknown | 1.04 | 25.05 | 0.51 | 25.04 |
| D8 | Unknown | 1.03 | 24.33 | 0.48 | 25.25 |
| D9 | Unknown | 1.00 | 25.21 | 0.49 | 25.27 |
| D10 | Unknown | 1.01 | 25.29 | 0.51 | 25.36 |
| D11 | Unknown | 0.99 | 25.20 | 0.53 | 24.58 |
| D12 | Unknown | 1.03 | 24.31 | 0.50 | 24.97 |
| E1 | Unknown | 1.00 | 25.17 | 0.51 | 25.35 |
| E2 | Unknown | 1.04 | 24.98 | 0.49 | 24.58 |
| E3 | Unknown | 1.04 | 24.86 | 0.49 | 24.97 |
| E4 | Unknown | 1.01 | 24.64 | 0.40 | 25.35 |

FIG. 9A

| E5 | Unknown | 0.73 | 28.31 | 0.50 | 25.28 |
|---|---|---|---|---|---|
| E6 | Unknown | 0.74 | 28.51 | 0.50 | 25.81 |
| E7 | Unknown | 0.76 | 28.31 | 0.49 | 25.56 |
| E8 | Unknown | 0.76 | 28.51 | 0.49 | 25.54 |
| E9 | Unknown | 0.60 | 28.49 | 0.50 | 25.55 |
| E10 | Unknown | 0.74 | 28.45 | 0.50 | 26.01 |
| E11 | Unknown | 0.72 | 28.25 | 0.48 | 25.54 |
| E12 | Unknown | 0.75 | 29.48 | 0.49 | 26.02 |
| F1 | Unknown | 0.77 | 30.11 | 0.48 | 25.30 |
| F2 | Unknown | 0.38 | 30.52 | 0.48 | 25.30 |
| F3 | Unknown | 0.41 | 29.87 | 0.51 | 25.16 |
| F4 | Unknown | 0.37 | 33.83 | 0.47 | 25.43 |
| F5 | Unknown | 0.39 | 31.79 | 0.48 | 25.77 |
| F6 | Unknown | 0.40 | 32.06 | 0.48 | 25.90 |
| F7 | Unknown | 0.41 | 31.16 | 0.50 | 26.03 |
| F8 | Unknown | 0.39 | 31.70 | 0.50 | 25.46 |
| F9 | Unknown | 0.41 | 31.29 | 0.48 | 25.53 |
| F10 | Unknown | 0.39 | 32.20 | 0.49 | 25.83 |
| F11 | Unknown | 0.41 | 31.73 | 0.50 | 25.91 |
| F12 | Unknown | 0.41 | 33.61 | 0.50 | 25.32 |
| G1 | Unknown | 0.39 | 30.86 | 0.48 | 25.32 |
| G2 | Unknown | 0.41 | 35.58 | 0.49 | 25.44 |
| G3 | Unknown | 0.39 | 32.36 | 0.50 | 25.57 |
| G4 | Unknown | 0.41 | 33.43 | 0.50 | 25.51 |
| G5 | Unknown | 0.40 | 29.50 | 0.48 | 25.55 |
| G6 | Unknown | 0.13 | 33.55 | 0.49 | 25.35 |
| G7 | Unknown | 0.086 | 29.86 | 0.48 | 25.28 |
| G8 | Unknown | 0.12 | 31.29 | 0.49 | 25.53 |
| G9 | Unknown | 0.088 | 32.20 | 0.49 | 25.01 |
| G10 | Unknown | 0.12 | 31.73 | 0.50 | 25.38 |
| G11 | Unknown | 0.10 | 33.61 | 0.52 | 25.45 |
| G12 | Unknown | 0.14 | 30.86 | 0.51 | 25.52 |
| H1 | Unknown | 0.05 | 35.58 | 0.51 | 25.04 |
| H2 | Unknown | 0.03 | 32.36 | 0.51 | 24.87 |
| H3 | Unknown | 0.03 | 33.43 | 0.52 | 24.65 |
| H4 | Unknown | 0.04 | 29.50 | 0.52 | 25.31 |
| H5 | Unknown | 0.045 | 33.55 | 0.51 | 24.84 |
| H6 | Unknown | 0.055 | 29.86 | 0.51 | 25.14 |
| H7 | Unknown | 0.040 | 29.57 | 0.49 | 25.15 |
| H8 | Unknown | 0.0009 | 40 | 0.51 | 24.97 |
| H9 | Unknown | 0.042 | 30.94 | 0.52 | 25.20 |
| H10 | Unknown | 0.05 | 30.29 | 0.48 | 25.17 |
| H11 | Unknown | 0.05 | 30.18 | 0.54 | 24.88 |
| H12 | Unknown | 0.04 | 31.26 | 0.54 | 25.19 |

FIG. 9B

SEQUENCE LISTING (1) GENERAL INFORMATION:

(iii) NUMBER OF SEQUENCES: 16

(2) INFORMATION FOR SEQ ID NO:1:

(i) SEQUENCE CHARACTERISTICS:
      (A) LENGTH: 26 base pairs
      (B) TYPE: nucleic acid
      (C) STRANDEDNESS: single
      (D) TOPOLOGY: linear (xi) SEQUENCE DESCRIPTION: SEQ ID NO:1:

CAACATCGAT TTCTTCCTCA TCTTCT      26

(2) INFORMATION FOR SEQ ID NO:2:

(i) SEQUENCE CHARACTERISTICS:
      (A) LENGTH: 19 base pairs
      (B) TYPE: nucleic acid
      (C) STRANDEDNESS: single
      (D) TOPOLOGY: linear (xi) SEQUENCE DESCRIPTION: SEQ ID NO:2:

GCCCCTGGTT GCTCCATGA      19

(2) INFORMATION FOR SEQ ID NO:3:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (xi) SEQUENCE DESCRIPTION: SEQ ID NO:3:

CAGCACAACT ACGCAGCGCC TCCT                                        24

(2) INFORMATION FOR SEQ ID NO:4:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:4:

TCCAACCGCC ACACTATCAA                                            20

(2) INFORMATION FOR SEQ ID NO:5:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (xi) SEQUENCE DESCRIPTION: SEQ ID NO:5:

CATCCGCACA CTATCTCATC GT                                        22

(2) INFORMATION FOR SEQ ID NO:6:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (xi) SEQUENCE DESCRIPTION: SEQ ID NO:6:

CAGCTCGTTG ATCTTCCGTT CTGGCA                                26

(2) INFORMATION FOR SEQ ID NO:7:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO:7:

TCCAACCCGC CACCCACTAT C                                          21

(2) INFORMATION FOR SEQ ID NO:8:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (xi) SEQUENCE DESCRIPTION: SEQ ID NO:8:

CAGGACGGGC GTTCCTTGC                                              19

(2) INFORMATION FOR SEQ ID NO:9:

(i) SEQUENCE CHARACTERISTICS:
    (A) LENGTH: 22 base pairs
    (B) TYPE: nucleic acid
    (C) STRANDEDNESS: single
    (D) TOPOLOGY: linear (xi) SEQUENCE DESCRIPTION: SEQ ID NO:9:

GTGGGTCGAA TGGGCAGGTA GC                                              22

(2) INFORMATION FOR SEQ ID NO:10:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (xi) SEQUENCE DESCRIPTION: SEQ ID NO:10:

ACTGAAGCGG GAAGGGACTG GCT                                             23

(2) INFORMATION FOR SEQ ID NO:11:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:11:

ATCCTGGACC AGGTTCCTGA                                                 20

(2) INFORMATION FOR SEQ ID NO:12:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO:12:

CGGTACAAGC TGCAACTGTT A                                               21

(2) INFORMATION FOR SEQ ID NO:13:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO:13:

TAGGCAGTAT TCCGAAATGA C                                               21

(2) INFORMATION FOR SEQ ID NO:14:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (xi) SEQUENCE DESCRIPTION: SEQ ID NO:14:

CGGATTGTAG TCTGCAACTC GACTA                                           25

(2) INFORMATION FOR SEQ ID NO:15:

(i) SEQUENCE CHARACTERISTICS:
        (A) LENGTH: 20 base pairs

```
         (B) TYPE: nucleic acid
         (C) STRANDEDNESS: single
         (D) TOPOLOGY: linear (xi) SEQUENCE DESCRIPTION: SEQ ID NO:15:

ACAAACCGAC TTCGGGCATT                                              20

(2) INFORMATION FOR SEQ ID NO:16:

(i) SEQUENCE CHARACTERISTICS:
         (A) LENGTH: 29 base pairs
         (B) TYPE: nucleic acid
         (C) STRANDEDNESS: single
         (D) TOPOLOGY: linear (xi) SEQUENCE DESCRIPTION: SEQ ID NO:16:

AATACGTTCT CGGGTCTTGT ACACACCGC                                    29
```

METHODS USING EXOGENOUS, INTERNAL CONTROLS AND ANALOGUE BLOCKS DURING NUCLEIC ACID AMPLIFICATION

FIELD OF THE INVENTION

The invention relates generally to the field of nucleic acid amplification, and more particularly, to methods of internal controls that verify the absence or presence of specific target sequences during the polymerase chain reaction.

REFERENCES

Agrawal, S. etal, "Site-specific functionalization of oligonucleotides for attaching two different reporter groups", Nucleic Acids Research, 18: 5419–5423 (1990).

Ambion Technical Bulletin, Ambion Inc., http://www.ambion.com.

Andrus, A. in Evaluating and Isolating Synthetic Oligonucleotides, (1992), Applied Biosystems, Inc., Foster City, Calif.

Andrus, A., "Chemical methods for 5' non-isotopic labelling of PCR probes and primers" (1995) in *PCR 2: A Practical Approach*, Oxford University Press, Oxford, pp. 39–54

Barany, F., "The Ligase Chain Reaction in a PCR World", PCR Methods and Applications 1:5–16 (1991).

Barany, F. "Genetic disease detection and DNA amplification using cloned thermostable ligase", Proc. Nat. Acad. Sci USA 88:189–193 (1991).

Beaucage, S. L. and Iyer, R. P. "Advances in the synthesis of oligonucleotides by the phosphoramidite approach", Tetrahedron 48:2223–2311 (1992).

Bergot etal, "Spectrally resolvable rhodamine dyes for nucleic acid sequence determination", U.S. Pat. No. 5,366,860, issued Nov. 22, 1994.

Bevan etal, "Sequencing of PCR-amplified DNA", PCR Methods and Applications, 1:222–228 (1992)

Blackburn, G. M. and Gait, M. J. Eds. "DNA and RNA structure" in *Nucleic Acids in Chemistry and Biology*, 2nd Edition, (1996) Oxford University Press, pp. 15–81.

Caruthers, M. and Beaucage, S., "Phsophoramidite compounds and processes" U.S. Pat. No. 4,415,732, issued Nov. 15, 1983.

Cardullo etal, "Detection of nucleic acid hybridization by non-radiative fluorescence resonance energy transfer", Proc. Natl. Acad. Sci., 85:8790–8794 (1988)

Clegg, R., "Fluorescence resonance energy transfer and nucleic acids", Meth. Enzymol., 211:353–388 (1992

Dieffenbach, C. W. and Dveksler, G. S. in *PCR Primer: A Laboratory Manual* (1995) Cold Spring Harbor Laboratory Press, pp. 13–14.

Egholm, M, Buchardt, O. Christensen, L, Behrens, C, Freier, S., Driver, D., Berg, R., Kim, S. "PNA hybridizes to complementary oligonucleotides obeying the Watson-Crick hydrogen bonding rules", Nature, 365:566–68 (1993).

Fung etal, "Method of detecting electrophoretically separated oligonucleotides", U.S. Pat. No. 4,855,225, issued Aug. 8, 1989.

Gelfand, D., Holland, P., Saiki, R., and Watson, R., "Homogeneous assay system using the nuclease activity of a nucleic acid polymerase", U.S. Pat. No. 5,210,015, issued May 9, 1993.

Gilliland etal, "Analysis of cytokine mRNA and DNA: Detection and quantitation by competitive polymerase chain reaction", Proc. Natl. Acad. Sci., 87:2725–2729 (1990)

Green etal, "Sequenced-tagged site (STS) content mapping of human chromosomes: Theoretical considerations and early experiences", PCR Methods and Applications, 1:77–90 (1991).

Hermanson, G. T., in *Bioconjugate Techniques,* (1996) Academic Press, San Diego, pp. 40–55, 643–671.

Higuchi, R., Fockler, C., Dollinger, G. and Watson, R., "Kinetic PCR: Real time monitoring of DNA amplification reactions" Biotechnology, 11:1026–30 (1993)

Higuchi, R., Dollinger, G., Walsh, P., and Griffith, R., "Simultaneous amplification and detection of specific DNA sequences" Biotechnology, 10:413–17 (1992)

Holland, P. M., Abramson, R., Watson, R. and Gelfand, D., "Detection of specific polymerase chain reaction product by utilizing the 5' to 3' exonuclease activity of Thermus aquaticus DNA polymerase" Proc. Natl. Acad. Sci., 88:7276–80 (1991).

Horn, T. and Urdea, M., "A chemical 5'-phosphorylation of oligodeoxyribonucleotides that can be monitored by trityl cation release", Tetrahedron Lett., 27: 4705–08 (1986)

Innis etal, in *PCR Protocols,* Academic Press, NY (1989)

Ju, J. etal, "Design and Synthesis of fluorescence energy transfer dye-labeled primers and their application for DNA sequencing and analysis", Analytical Biochemistry, 231:131–140 (1995).

Keller, G. and Manak, M., in *DNA Probes, Second Edition,* (1993), Stockton Press, New York.

Kricka, L., in *Nonisotopic DNA Probe Techniques* (1992), Academic Press, San Diego, pp. 3–28.

Lawyer, F. C., Stoffel, S., Saiki, R., Myambo, K., Drummond, R. and Gelfand, D., "Isolation, characterization, and expression in *Escherichia coli* of the DNA polymerase gene from the extreme thermophile, *Thermus aquaticus." J. Biol. Chem.* 264:6427–37 (1989).

Lee, L. G., Connell, C., and Bloch, W., "Allelic discrimination by nick-translation PCR with fluorogenic probes", Nucl. Acids Res., 21:3761–66 (1993)

Livak, K., Flood, S., Mannaro, J., Giusti, W., and Deetz, K., "Oligonucleotides with fluorescent dyes at opposite ends provide a quenched probe system useful for detecting PCR product and nucleic acid hybridization". PCR Methods and Applications, 4:357–362 (1995)

Livak, K. U.S. Ser. No. 08/657,689 and WO 97/46708, "Passive internal references for the detection of nucleic acid amplification products"

Livak, K., Flood, S., Marmaro, J. "Method for Detecting Nucleic Acid Amplification Using Self-Quenching Fluorescence Probe", U.S. Pat. No. 5,538,848, issued Jul. 23, 1996.

Livak, K., Marmaro, J., and Todd, J., "Towards fully automated genome-wide polymorphism screening" Nature Genetics, 9:341–42 (1995).

Longo, M. C., Berninger, M. S., and Hartley, J. L. (1990) "Use of uracil DNA glycosylase to control carryover contamination in polymerase chain reactions" Gene, 93:125–28.

Lyamichev, V., Brow, M., Dahlberg, J., "Structure-specific endonucleolytic cleavage of nucleic acids by eubacterial DNA polymerases". Science, 260:778–83 (1993).

McPherson, M. J., Quirke, P., and Taylor, G. R. in *PCR 2: A Practical Approach* (1995) Oxford University Press, Oxford, pp. 7, 19.

McPherson, M. J., Quirke, P., and Taylor, G. R. in *PCR: A Practical Approach, Volume I* (1991) Oxford University Press, Oxford, pp. 46, 199.

Menchen etal, "4,7-Dichlorofluorescein dyes as molecular probes", U.S. Pat. No. 5,188,934, issued Feb. 23, 1993.

Mullah B. and Andrus, A., "Automated synthesis of double dye-labeled oligonucleotides using tetramethylrhodamine (TAMRA) solid supports", Tetrahedron Letters, 38: 5751–5754 (1997).

Mullah, B., Livak, K., Andrus, A. and Kenney, P., "Efficient synthesis of double dye-labeled oligodeoxyribonucleotide probes and their application in a real time PCR assay", Nucl. Acids Res. 26:1026–1031 (1998).

Nielsen, P. E., Egholm, M., Berg, R. H., and Buchardt, O., "Sequence-selective recognition of DNA by strand displacement with a thymidine-substituted polyamide", Science 254:1497–1500 (1991).

Orum, H., Nielsen, P., Egholm, M., Berg, R., Buchardt, O., and Stanley, C. "Single base pair mutation analysis by PNA directed PCR clamping", Nuc. Acids Res 21:5332–36 (1993).

Ozaki, H. and McLaughlin, L., "The estimation of distances between specific backbone-labeled sites in DNA using fluorescence resonance energy transfer", Nucleic Acids Research, 20: 5205–5214 (1992)

Perseptive Biosystems, "Identifying point mutations by PNA-directed PCR clamping" (1995).

Ruth, J., "Single-stranded labelled oligonucleotides, reactive monomers and methods of synthesis" U.S. Pat. No. 4,948,882, issued Aug. 14, 1990.

Theisen, P., McCollum, C., and Andrus, A. "Fluorescent dye phosphoramidite labelling of oligonucleotides", *Nucleic Acid Symposium Series No. 27*, Oxford University Press, Oxford, pp. 99–100 (1992).

Tsai S-J, and Wiltbank M. C., "Quantification of mRNA Using Competitive RT-PCR with Standard Curve Methodology" Biotechniques 21:5:862–866 (1996).

Tyagi, S. and Kramer, F. R., "Molecular Beacons: Probes that fluoresce upon hybridization", Nature BioTechnology, 14:303–08 (1996).

Tyagi, S. and Kramer, F. R., "Detection probes, kits, and assays" Intl. Publ. WO 97/39008.

Urdea etal, "Nucleic acid probes" U.S. Pat. No. 5,093,232, issued Mar. 3, 1992.

Van der Laan, A. etal, "A Convenient automated solid-phase synthesis of PNA-(5')-DNA-(3')-PNA chimera", Tetrahedron Lett., 38:2249–52 (1997).

Vinayak, R. etal, "Automated chemical synthesis of PNA-DNA chimera on a nucleic synthesizer", Nucleosides & Nucleotides, 16:1653–56 (1997).

Walker, G. etal, "Strand displacement amplification—an isothermal, in vitro DNA amplification technique", Nucleic Acids Research, 20: 1691–1696 (1992).

Walker, G., Little, M., Nadeau, J. and Shank, D., "Isothermal in vitro amplification of DNA by a restriction enzyme/DNA polymerase system" Proc. Natl. Acad. Sci. 89:392–96 (1992).

Wang, M., Doyle, M. V., and Mark, D. F., "Quantitation of mRNA by the Polymerase Chain Reaction", Proc. Natl. Acad. Sci. USA 86:9717–9721 (1989).

Woo etal., "Rhodamine phosphoramidite compounds", U.S. Pat. No. 5,231,191, issued Jul. 27, 1993.

Woo, S. and Fung, S., "Solid support reagents for the synthesis of 3'-nitrogen containing polynucleotides" U.S. Pat. No. 5,552,471, issued Sept. 3, 1996.

Zimmermann, K., Schogl, D., Plaimauer, B., and Mannhalter, J. W., "Quantitative Multiple Competitive PCR of HIV-1 DNA in a Single Reaction Tube", BioTechniques 21:481–484 (1996).

BACKGROUND

Nucleic acid amplification, and the polymerase chain reaction (PCR) in particular, has become an important research tool, with applications in cloning, analysis of genetic expression, DNA sequencing, genetic mapping, drug discovery, and the like (Gilliland etal, 1990; Bevan etal, 1992; Green etal, 1991). Descriptions of, and guidance for conducting, PCR is provided in extensive literature on the subject (Innis etal, 1989; McPherson etal, 1991; McPherson etal, 1995).

Automated instrumentation has been developed for carrying out nucleic acid amplifications, most commonly automated thermal cyclers for conducting PCR and the like. Important design goals fundamental to PCR instrument development have included fine temperature control, minimization of sample-to-sample variability in high-throughput, highly multiplexed-sample thermal cycling, automation of pre- and post-PCR processing steps, high-speed cycling, minimization of sample volumes, real time measurement of amplification products, minimization of cross-contamination or sample carryover, and the like. In particular, the design of instruments that permit PCR to be carried out and monitored in real time is highly desirable. Reaction chambers that remain closed during amplification and analysis are desirable for preventing cross-contamination (Higuchi etal, 1992; Higuchi etal, 1993; Holland etal, 1991).

Methods, reagents, and kits of reagents that facilitate multi-channel pipetting or robotic dispensing are desirable. A limited number of automated pipetting and dispensing steps will minimize errors and ambiguous results. Clearly, the successful realization of these design goals would be especially desirable in the analysis of diagnostic samples, where a high frequency of false positives and false negatives would severely reduce the value of the PCR-based procedure.

Fluorescence-based approaches to provide real time measurements of amplification products during a PCR (Holland etal, 1991) have either employed intercalating dyes (such as ethidium bromide) to indicate the amount of double stranded DNA present (Higuchi, 1992; Higuchi, 1993; Gelfand etal, 1993) or probes containing reporter-quencher pairs ("TaqMan®", exonuclease assay) that are cleaved during amplification to release a fluorescent signal that is proportional to the amount of double stranded DNA present (Livak 1996). The polymerase that conducts primer extension and amplifies the polynucleotide also possesses a 5'→3' exonuclease activity that serves to cleave the probe. In the exonuclease assay, a "reporter" dye and a "quencher" dye are attached to an oligonucleotide probe which is complementary to the target DNA. The dyes are selected and arranged to interact through a fluorescence resonance energy transfer (FRET) process (Clegg, R., 1992). The reporter is a luminescent compound that can be excited either by chemical reaction, producing chemiluminescence, or by light absorption, producing fluorescence (FIG. 1). The quencher can interact with the reporter to alter its light emission, usually resulting in the decreased emission efficiency of the reporter. This phenomenon is called quenching. The efficiency of quenching is a strong function of the distance between the reporter molecule and the quencher molecule. Thus, in a nucleic acid hybridization assay, detection of a hybridization event is accomplished by designing an energy transfer system in which the spacing between a reporter and a quencher is modulated as a result of the hybridization. Two examples of systems that perform the exonuclease assay and other quantitation, fluorescent-based arrays are the ABI PRISM™ 7700 and ABI PRISM™ 7200 Sequence Detection Systems (Perkin-Elmer).

The exonuclease assay of nucleic acid amplification employing reporter-quencher probes (Lee etal, 1993; Livak etal, 1995) gives direct detection of polymerase chain reaction (PCR) products with no downstream sample processing. The quencher is released from its close proximity to the reporter upon cleavage so that the signal from the reporter is no longer quenched. An increase in fluorescence occurs which correlates directly and proportionally with the increase in copies of the PCR product. By using real-time or end-point analysis, detection and quantitation of PCR products can be obtained by measuring the increase in fluorescence of cleaved, self-quenching fluorescent probes.

Release of fluorescence can be detected and measured by laser-induced fluorescence with an optical-fiber probe in a non-invasive, closed reaction chamber. The assay is conducted by a high-throughput, data sampling routine during the course of PCR thermal cycling (real-time analysis) or at the end of PCR (end-point analysis). Automated quantitation using PCR is highly desirable. Manual methods rely on end-point electrophoresis of an aliquot of the PCR and spectroscopic or densitometric quantitation. Real time monitoring of PCR permits far more accurate quantitation of starting target DNA concentrations in multiple-target amplifications than manual end-point methods. With calibrated, internal controls, the relative values of close concentrations can be resolved by factoring the history of the relative concentration values during the PCR. Real time monitoring of target with internal controls is desirable.

Internal and/or parallel tests that confirm conditions for amplification of the target are desirable as control tests. When used in a high-throughput format, such as 96 well, microtitre plate configurations, PCR often is plagued by false positives due to template contamination from adjacent wells, pipetting errors, or aerosol transmission. In addition, PCR suffers from false negative results when enzyme inhibitors are present in the target samples or when reagents are missing or degraded. Therefore, control amplification tests are desirable.

Positive amplification control tests give a detectable product derived from a component that is separate and distinct from the target. Detection of the positive control product indicates that amplification is viable and operative within the reaction chamber. Positive amplification control tests which give no detectable product from the control components, indicate conditions within the reaction chamber that do not allow amplification. Another desirable feature of amplification control is to "turn off" the positive control signal with the addition of a negative or "blocking" element to other reaction chambers during the assay, allowing the measurement of background.

Internal amplification controls are to be distinguished from "passive" internal reference molecules (Livak, Ser. No. 08/657,689) which provide for signal and detection corrections. Passive internal references, such as non-complementary, reporter-quencher molecules do not hybridize to target or other polynucleotides, are not consumed or act as substrates for enzymes, and do not undergo chemical or enzymatic reactions of any sort. Thus, passive internal references do not provide verification or indication of conditions for amplification, within the reaction chamber.

In addition to the above limitations and problems associated with signal and detection, a passive internal reference does not address the very common issues of; (i) contamination of target or other reagents with foreign DNA, (ii) inhibition of PCR, and (iii) confirming amplification efficiency within the reaction chamber. Reporter-quencher probe assays with internal fluorescence-generating controls are needed to provide accurate, precise, and sensitive measurements of changes in fluorescence that are attributable solely to formation of the amplification product.

Control amplification reactions are necessary for (i) normalization of quantitation results, (ii) detection of amplification inhibitors in the target and other reagents, and (iii) to establish background signal levels. A pervasive difficulty is keeping amplification of the control polynucleotide from interfering with target amplification or detection of the product. Internal control polynucleotides (ICP) undergo amplification within the same reaction chamber as the known or unknown target polynucleotide, imparting convenience in preparing samples and measuring results. The ICP may be endogenous, i.e. from the same source, genome, chromosome, gene, plasmid, or fragment as the target. Endogenous ICP are subject to amplification inhibitors and can therefore give a false negative signal. Endogenous ICP also may have priming sites for target primers and therefore give a false positive signal. In fact, endogenous ICP systems may share one or more primers with the target. Exhaustion of shared primers leads to inaccurate PCR quantitation and limited dynamic range. Another negative feature of endogenous ICP is the necessity to select, design, and purify ICP, ICP primers, and ICP self-quenching probe for each target to ensure compatibility and viable amplification. A universal exogenous ICP which is not derived from the same source, etc. as the target is therefore desirable, to avoid these disadvantages.

In addition to the positive control amplification, it is desirable to have separate, parallel negative control tests to establish a background signal level for quantitative systems such as the exonuclease assay. By "switching off" the control amplification, the fluorescence of the intact self-quenching probe of the internal control polynucleotide can be monitored and subtracted as a baseline value from samples undergoing normal amplification. Previous attempts at negative control background measurement have entailed; (i) deletion of essential components of amplification, such as magnesium, DNTP, and enzyme, or (ii) addition of amplification inhibitors such as sodium dodecyl sulfate (SDS) or EDTA. All of these attempts suffer from the disadvantage of changing, distorting, or obscuring fluorescent signal generation or detection.

Most techniques used for total RNA isolation yield RNA with significant amounts of genomic DNA contamination (Ambion). Reverse transcription, polymerase chain reaction (RT-PCR) is a popular method for analyzing low abundance mRNA from limiting amounts of tissue and the quantitative analysis of gene expression. Because the PCR step involves an exponential amplification, small tube-to-tube variations in amplification efficiency can translate into dramatic differences in the yield of final product and gross errors in estimation of initial abundance. A frequent cause of concern among investigators performing quantitative RT-PCR is inaccurate data caused by DNA contamination in RNA preparations. PCR cannot discriminate between cDNA targets synthesized by reverse transcription and genomic DNA contamination. Although DNA contamination is easily detected by performing a 'no-RT' negative control, there is no satisfactory and comprehensive solution to contamination and inhibition which the present invention provides. The conventional methods of RT-PCR quantitative analysis (Wang etal, 1989; Tsai etal, 1996; Zimmermann etal, 1996)

are all gel-based assays, which rely on imprecise and subjective visualization techniques.

In view of the limitations and deficiencies of conventional controls for the quantitation and detection of nucleic acid amplification products, it is of interest to develop non-gel based internal control methods that provide both negative and positive indications amplification. The invention described herein provides for such internal control reagents, kits, and methods.

SUMMARY

The present invention is directed towards novel methods and a kit of reagents for quantitating nucleic acid amplification of control DNA in the presence of, and concurrently with, nucleic acid amplifications of known and unknown target DNA.

It is an object of certain embodiments of the present invention to provide a method of conducting nucleic acid amplification reactions in a single reaction chamber whereby internal control primers hybridize to an internal control polynucleotide and target primers hybridize to a target polynucleotide, and amplification of polynucleotides occurs by polymerase chain extension, thermal melting, and hybridization. Internal control polynucleotides are comprised of DNA or RNA and are not sequence-homologous to target polynucleotides. Internal control polynucleotides do not allow amplification by target primers or hybridization with target probes. The amplification product resulting from amplification of the internal control polynucleotide with internal control primers will typically be from 50–500 bp in length. The amplicon will contain an internal site complementary for hybridization of the internal control probe. An internal control polynucleotide comprised of RNA may be a substrate for reverse-transcriptase and result in the production of a cDNA copy.

It is another object of certain embodiments of the present invention to provide internal control reagents and methods that detect the presence of PCR inhibitors in the target and other components in the PCR mixture. The internal controls will have the properties of being easy to dispense, i.e. a minimum of pipetting operations and conducive to robotic automation in the conventional 96-well microtitre plate format. The internal control reagents should not decrease PCR amplification efficiency of the target polynucleotide. Both negative and positive internal control signals should give distinct and operative results. A positive internal control signal can discriminate a true negative target signal from a false negative. Measurement of a negative internal control signal gives the background which is subtracted from the positive internal control signal. The fluorescence of the reporter on the internal control probe is measured so as to normalize the reaction for such amplification factors that vary from reaction to reaction. Thus by examining the fluorescent signal from the internal control probe, the effects of most sources of PCR inhibition are identified.

Reporter-quencher probe assays including the subject internal control reagents may be used in conjunction with a variety of nucleic acid amplification systems. Generally, the assays require either the use of a nucleic acid polymerase with exonuclease activity or a population of double stranded DNA which increases during the course of the reaction being monitored. Exemplary amplification schemes that may be employed with the system of the invention include PCR, ligase-based amplification schemes, such as ligase chain reaction, LCR (Barany, 1991), Q-beta replicase-based amplification schemes, strand displacement amplification (SDA) schemes (Walker etal, 1992; Keller, 1993).

An exogenous ICP is selected and designed to have no sequence homology with any known target from inspection of sequence databanks. The exogenous ICP is DNA or RNA of 50–500 bp in length. The exogenous ICP is added to the amplification reagent kit, along with ICP primers and self-quenching probe, in known amounts to consistently yield a known amount of fluorescent signal. The exogenous ICP can verify amplification conditions within a reaction chamber to establish a true negative for the presence of target DNA.

It is yet another object of certain embodiments of the present invention to provide self-quenching fluorescence probes with different and non-homologous sequences for hybridization to the internal portions of target and internal control polynucleotides. Since the internal control polynucleotide (ICP) is designed or selected to have minimal homology with any known target polynucleotide, the internal control probe will hybridize only to ICP and not to target polynucleotide. Similarly, the target probe will hybridize only to target polynucleotide, and not to ICP. Self-quenching probes exist in at least one single-stranded conformation when unhybridized such that the quencher dye quenches the fluorescence of the reporter dye. When hybridized to polynucleotides, the probes exist in at least one conformation where the fluorescence of the reporter dye is unquenched and the fluorescence intensity of reporter dye is greater than the fluorescence intensity of the quencher dye when the probe is hybridized to polynucleotide. Nucleic acid polymerase can substantially digest the probes during amplification to separate the reporter dye from the quencher dye. Fluorescence from the cleaved reporter dye corresponds to the occurrence of nucleic acid amplification. Fluorescence may also accrue based on hybridization of the probe to complementary target or ICP. The target and internal control probes are labelled with different and spectrally resolvable reporter moieties when used in the same reaction chamber. The respective emission spectra from the reporter moieties with a reaction chamber must be sufficiently non-overlapping so that separate emission contributions can be resolved. The separate peaks may be quantitated, correlating to the relative amounts of amplification products, i.e., target and internal control polynucleotides.

Clearly, the system may be generalized to include a plurality of fluorescent reporters, e.g. to monitor the simultaneous amplification of several target nucleic acids in a single reaction, so that a plurality of fluorescent intensity ratios are monitored. Such multi-reporter systems are advantageous in applications requiring the analysis of multiple amplifications occurring in a single reaction chamber. In such systems, each of the reporter molecules produce emissions which are spectrally resolvable from the emissions from any of the other reporters. The particular quencher used with each reporter can be the same or different, depending on the spectral properties of the quencher and reporter. Several spectrally resolvable dyes suitable for use in such embodiments are disclosed in Fung etal; Menchen etal; Bergot etal; and like references.

In a preferred embodiment of the self-quenching fluorescence probe, the reporter dye is separated from the quencher dye by at least 12 nucleotides, the reporter dye is attached at the 5' terminus or 3' terminus of the self-quenching fluorescence probe, and the quencher dye is attached at the 5' terminus or 3' terminus. In another preferred embodiment, a first self-quenching fluorescence probe is complementary to the internal control polynucleotide and a second self-quenching fluorescence probe is complementary to the target polynucleotide. Additionally, the reporter dye of the first self-quenching fluorescence probe is spectrally resolvable from the reporter dye of the second self-quenching fluorescence probe. Preferably, in this embodiment, an excitation beam is generated from the 488 nm emission line of an argon ion laser to induce fluorescence in the reporter dye. Fluorescence emission from the reporters and quenchers can be detected from 500 to 650 nm. Fluorophores in a reaction chamber can be discriminated when the emission maxima are sufficiently different and the emission bandwidth is sufficiently narrow.

Preferred embodiments of reporter moieties are fluorescein dyes with the general structure and numbering system below, where L is a linker.

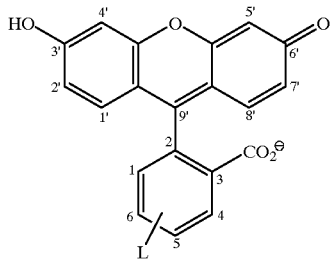

Preferred embodiments of fluorescein reporter dyes are selected from the group consisting of 5-carboxyfluorescein (5-FAM), 6-carboxyfluorescein (6-FAM), 2',4',1,4,-tetrachlorofluorescein (TET), 2',4',5',7', 1,4-hexachlorofluorescein (HEX), and 2',7'dimethoxy-4',5'-dichloro-6-carboxyrhodamine (JOE) (FIG. 2). Other embodiments of reporter moieties are cyanine dyes, dansyl derivatives, and the like.

Preferred embodiments of quencher moieties are; (i) rhodamine dyes selected from the group consisting of tetramethyl-6-carboxyrhodamine (TAMRA), and tetrapropano-6-carboxyrhodamine (ROX)., and (ii) DABSYL, DABCYL, cyanine, anthroquinone, nitrothiazole, and nitroimidazole compounds and the like (FIG. 3). Rhodamine dyes may bear the general structure and numbering system below, where L is a linker.

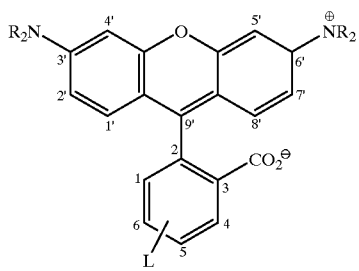

Fluorescein and rhodamine derivatives of the present invention may be substituted at one or more of the numbered positions above.

It is another aspect of the present invention to provide an oligonucleotide or nucleic acid analog, referred hereafter as a "block", that is complementary to the ICP and which is not extendable during nucleic acid amplification. The block may hybridize to any portion of the ICP with an equal or greater affinity than the internal control primers and prevent amplification of the ICP. Addition of the block to PCR will effect a negative result to the internal control. No amplification product from the ICP will result, as detected by the absence or minimal background of fluorescence from the internal control probe. Fluorescence from the internal control probe is measured at the emission maxima, e.g., occurring between 500–650 nm of the internal control reporter. The reporter on the target probe is chosen to have little or no spectral overlap with the reporter of the internal control probe. Therefore the reporter on the target probe can be measured independently from and concurrently with the reporter on the internal control probe within a single reaction chamber.

The block may be comprised of modifications to the internucleotide linkage, the sugar, or nucleobase moieties of a DNA primer to render it non-extendable by polymerase. An example of a suitable modification is a 3' phosphate group. Analogs of DNA may be employed as the block, such as, 2-aminoethylglycine, peptide-nucleic acid (PNA) and other amide-linked oligomers; 2'-O-methyl and other 2'-O-alkyl oligoribonucleotides; phosphorothioate and other phosphate analogs; and the like. The block is selected for several properties, including (i) high specificity, (ii) high affinity, (iii) non-extendability, (iv) chemical stability, (v) non-interference with amplification. In a preferred embodiment, the block is a PNA (peptide-nucleic acid) oligomer (Nielsen, P. E. etal). To improve solubility and lower aggregation effects, the PNA block may be conjugated with hydrophilic labels, such as polyethyleneoxy, peptides, nucleic acids, nucleic acid analogs, and the like.

PNA has been used in PCR as a "clamping element" for single base-pair mutation analysis (Orum etal). In this report, PNA suppresses amplification of complementary target sequences, typically wild-type, and allows the selective amplification of low-copy number or mutant target sequences with competing DNA primers.

Certain preferred embodiments of the present invention include methods for the endpoint and real-time measurements of amplification product formation. In an end-point mode, the fluorescence measurement is performed after the amplification reaction is complete, e.g., after all or substantially all of the amplification cycles of a PCR reaction have been completed. In a real-time mode, fluorescence measurements is performed multiple times during the amplification reaction, e.g., after each thermocycle of a PCR process. The real-time mode is preferred when a quantitative measure of the initial amount of target nucleic acid is required, e.g., the copy-number of pathogen nucleic acid present in a blood sample.

Fluorescent measurements may be used to verify the operability of PCR in the target vessel. The use of the internal control reagents of the invention permits the assignment of a near-zero background level of fluorescence for high-sensitivity tests, e.g. low copy-number or rare genes. The use of the internal control reagents of the invention permits the simultaneous use of multiple reporter-quencher probes in reporter-quencher probe assays.

It is an object of the invention to provide a method for accurate, real time monitoring of nucleic amplification reactions by providing apparatus and fluorescent reagents for generating a stable fluorescent signal proportional to the amount of amplification product. The availability of data showing the progress of amplification reactions leads to more accurate estimates of relative starting concentrations of target nucleic acids, to rapid assessment of the efficiency of the amplification reactions, and opens the possibility of reduced reagent usage and feedback reaction control.

It is an object of the present invention to provide a kit consisting of reagents required for nucleic acid amplification reactions for practicing the improved amplification methods of the invention. Kits make the practice of the claimed methods more reproducible and easier to perform. Kits may supply reagents in pre-measured amounts so as to simplify the performance of the subject methods. Furthermore, kits typically contain detailed instructions for carrying out the methods of the invention. In one embodiment of the invention, the kit comprises an internal control polynucleotide, internal control primers, a non-extending oligonucleotide or nucleic acid analog complementary to the internal control polynucleotide, target primers, a nucleic acid polymerase having 5'→3' nuclease activity, self-quenching fluorescence probes including reporter and quencher moieties, nucleotide 5'-triphosphates. The kits of the invention may further comprise additional reagents that are necessary for performing the subject methods, such reagents include, but are not limited to uracil N-glycosylase (UNG), buffers, molecular size standards, wax beads, and the like.

It is an object to employ the methods of the invention to sample tracking and signal calibration at the point of target sample extraction, isolation, or purification. For these purposes, internal control reagents comprised of ICP, internal control primers and probe may be added to crude sample preparations.

It is an object to employ the methods of the invention to reverse-transcriptase/PCR on mRNA samples, especially for low copy-number genes.

It is an object to employ the methods of the invention to allelic discrimination of polymorphic samples. Variations of a gene can be distinguished at the level of single base-pair differences of inherited alleles by the exonuclease assay (Lee etal, 1993).

It is an object to employ the methods of the invention to plus/minus, target-specific assays for pathogen detection, whereby one pair, or a limited plurality of pairs, of primers and a single reporter-quencher target probe are components of an amplification kit. The kit will also contain the internal control reagents and other components necessary for amplification. Measured aliquots from the kit can be dispensed in a high-throughput or automated manner to locations in a spatially-addressable test holder. Locations can be wells, sites, or surface arrays. The preferred embodiment of the holder is a microtitre well tray. The preferred embodiment of the locations are wells in a microtitre well tray. Typical location density is 96 wells in an 8×12 configuration of wells conforming to the accepted industry standards. Materials for the locations of the holder may be polymeric, metallic, glass, or ceramic. Target samples can be dispensed in a high-throughput or automated manner to the locations before or after delivery of the kit components.

BRIEF DESCRIPTION OF THE DRAWINGS

FIG. 8 Detection of E. Coli 01 57:H7. Exonuclease assay results from Example 4.

FIG. 9 Detection of Mycoplasma synoviae DNA. Exonuclease assay results from Example 5

Figure 1:
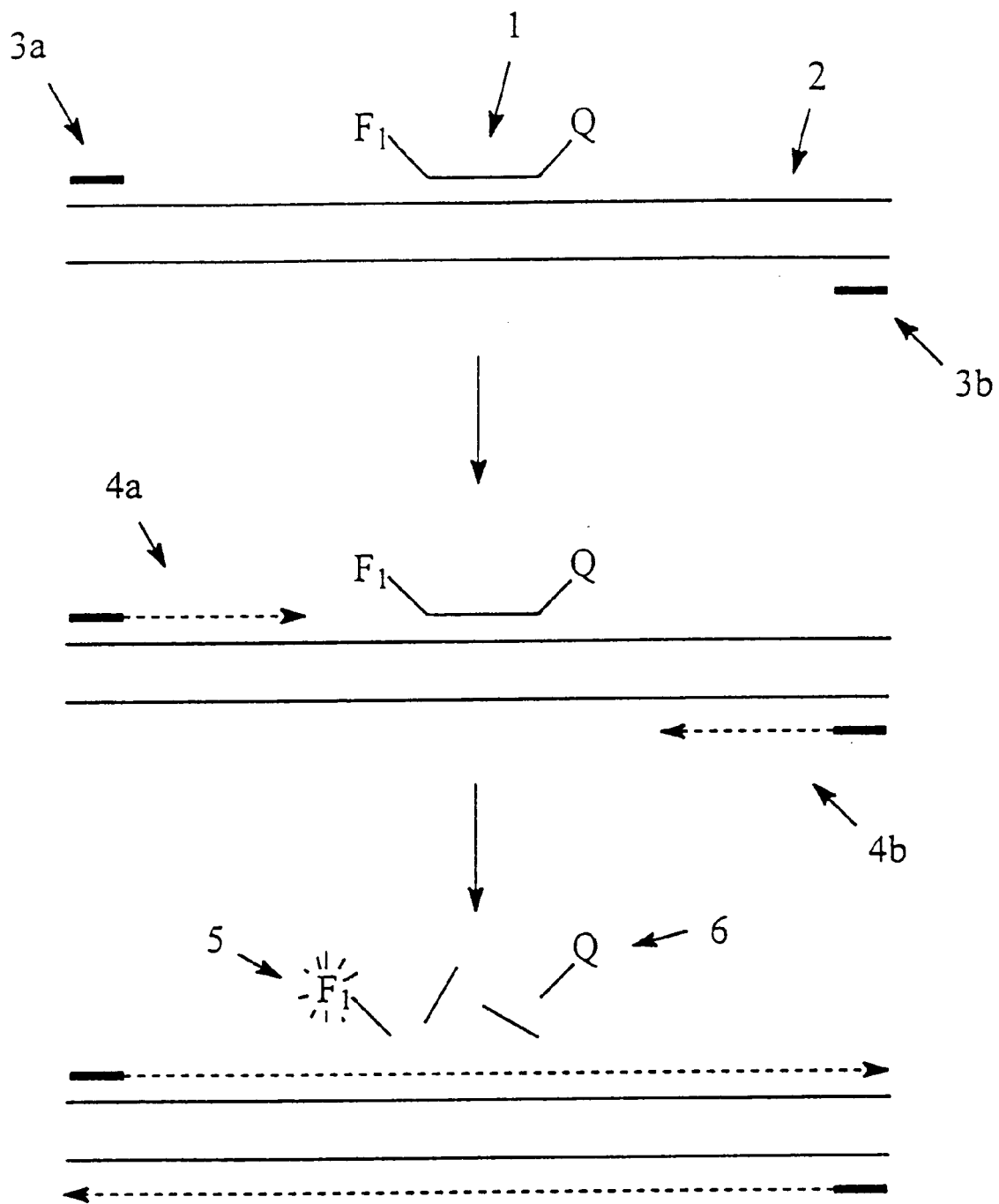
FIG. 1 Exonuclease assay target polynucleotide with self-quenching probe
Figure 2:
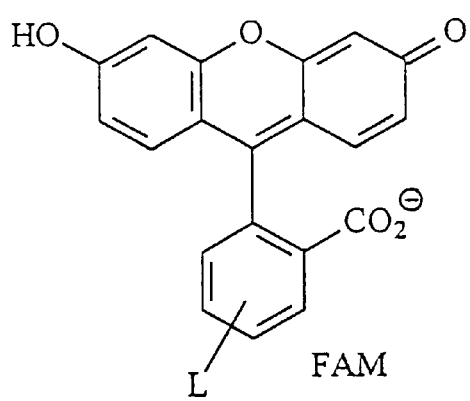
FIG. 2 Fluorescein reporter structures: FAM, TET, HEX, JOE
Figure 2:
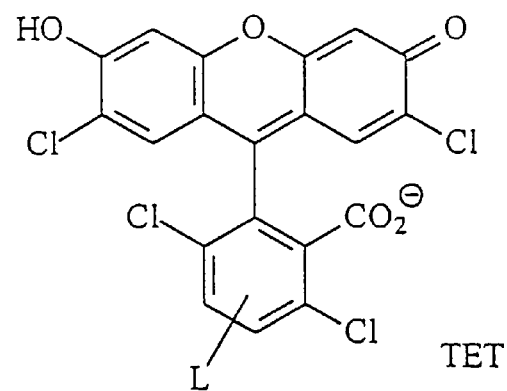
Figure 2:
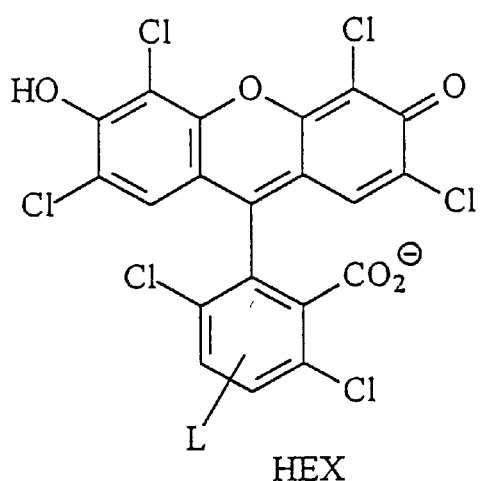
Figure 2:
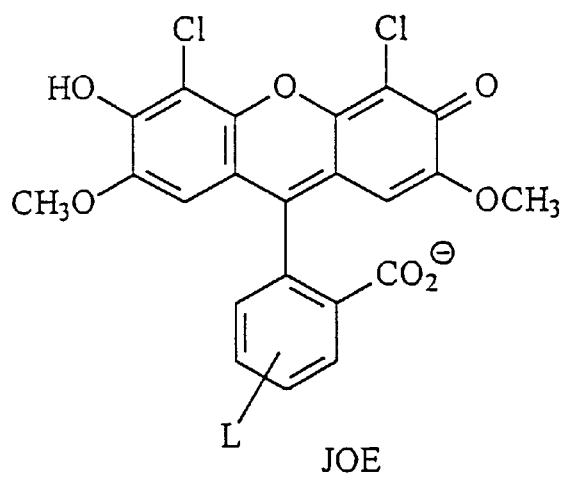
Figure 3:
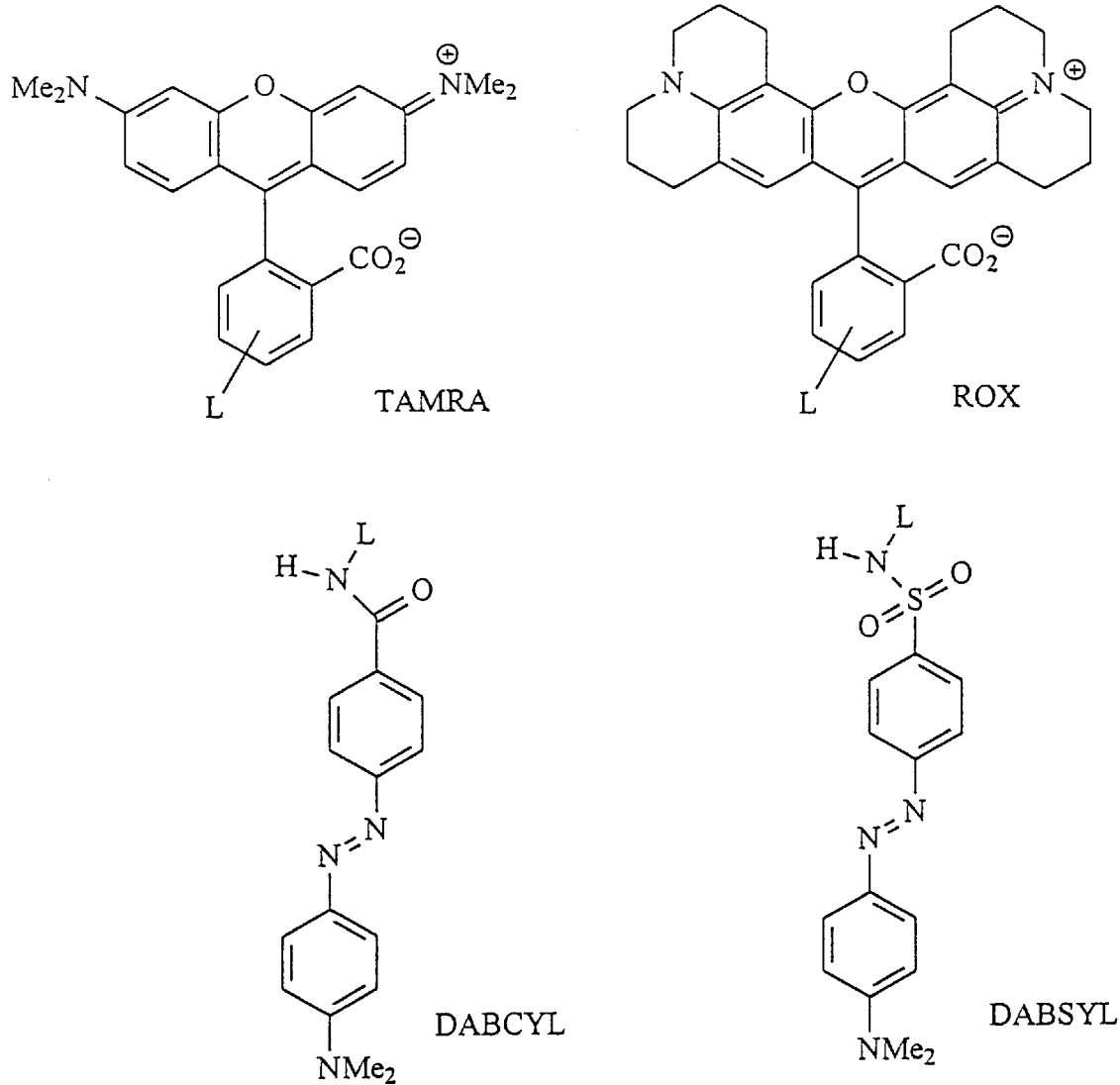
FIG. 3 Quencher structures: TAMRA, ROX, DABCYL, DABSYL

Well: location in 96 well format (FIG. 7)

Type: NAC—no amplification control, NTC—no template control, Unknown

Sample: target copy number by dilution, or negative

PCR: positive (+) or negative (−) result

Rn: reporter minus NTC (A7–A12)

Ct: threshold cycle number; PCR cycle number at which fluorescene is distinguishable from background

DETAILED DESCRIPTION OF THE PREFERRED EMBODIMENTS

Reference will now be made in detail to the preferred embodiments of the invention, examples of which are illustrated in the accompanying drawings. While the invention will be described in conjunction with the preferred embodiments, it will be understood that they are not intended to limit the invention to those embodiments. On the contrary, the invention is intended to cover alternatives, modifications, and equivalents, which may be included within the invention as defined by the appended claims.

I. DEFINITIONS

Unless stated otherwise, the following terms and phrases as used herein are intended to have the following meanings:

"Polynucleotide" or "oligonucleotide" refer to linear polymers of natural nucleotide monomers or analogs thereof, including double and single stranded deoxyribonucleotides "DNA", ribonucleotides "RNA", α-anomeric forms thereof, and the like. In other words, an "oligonucleotide" is a chain of deoxyribonucleotides or ribonucleotides, that are the structural units that comprise deoxyribonucleic acid (DNA) and ribonucleic acid (RNA), respectively.

"Nucleotide" is the monomer unit in biopolymer nucleic acids, such as DNA or RNA. A nucleotide is composed of three moieties: sugar, phosphate, and nucleobase (Blackburn, M., 1996). When part of a duplex, nucleotides are also referred to as "bases" or "base pairs". The most common naturally-occurring nucleobases, adenine (A), guanine (G), uracil (U), cytosine (C, and thymine (T) bear the hydrogen-bonding functionality that binds one nucleic acid strand to another in a sequence specific manner. "Nucleoside" refers to a nucleotide that lacks a phosphate dye. Usually the nucleoside monomers are linked by phosphodiester linkages, where as used herein, the term "phosphodiester linkage" refers to phosphodiester bonds or bonds including phosphate analogs thereof, including associated counter-ions, e.g., $H^+$, $NH^+$, $Na^+$, and the like. Polynucleotides typically range in size from a few monomeric units, e.g. 8–40, to several thousand monomeric units. Most molecular biology applications for polynucleotides require unique sequences of 15–30 nucleotides in length. Whenever a DNA polynucleotide is represented by a sequence of letters, such as "ATGCCTG," it will be understood that the nucleotides are in 5'→3+ order from left to right and that "A" denotes deoxyadenosine, "C" denotes deoxycytidine, "G" denotes deoxyguanosine, and "T" denotes thymidine, unless otherwise noted.

"Watson/Crick base-pairing" and "Watson/Crick complementarity" refer to the pattern of specific pairs of nucleotides, and analogs thereof, that bind together through hydrogen bonds, e.g. A pairs with T and U, and G pairs with C.

"Oligonucleotide analogs" are polymeric analogs of DNA and RNA made by chemical synthesis from monomeric nucleotide analog units, and possessing some of the qualities and properties associated with nucleic acids.

"Attachment site" refers to the atom on an oligonucleotide to which is attached the linker.

"Linker" refers to one or more atoms comprising a chain connecting an oligonucleotide and a label.

"Chimera" as used herein refers to an oligonucleotide including one or more nucleotide and one or more nucleotide analog units. The monomer units are linked through phosphodiester and phosphodiester analog linkages.

"Phosphodiester analog" refers to analogs of natural phosphodiester 3',5'-internucleotide linkages differing in their composition and/or location of attachment to a nucleotide, including but not limited to 2',5'-linkage, 3',3'-linkage, 5',5'-linkage, methyl phosphonate, alkylated phosphotriester, 3'-N-phosphoramidate, and PNA.

"Lower alkyl", "lower alkylene" and "lower substituted alkylene" refers to straight-chain, branched, or cyclic groups consisting of 1–12 carbon atoms.

"Label" refers to a group covalently attached at one or both termini of the nucleobase oligomer. The label is capable of conducting a function such as giving a signal for detection of the molecule by such means as fluorescence, chemiluminescence, and electrochemical luminescence (Kricka, L.). Alternatively, the label allows for separation or immobilization of the molecule by a specific or non-specific capture method (Andrus, A., 1995).

"Energy transfer" and "fluorescence quenching" refer to a processes whereby energy is removed from an electronically excited luminescent "reporter" molecule by a "quencher" molecule, thereby returning the reporter molecule to its ground state without the emission of light from the reporter molecule. The reporter molecule may be excited to one of its higher energy levels by any of a number of process, including light absorption and chemical reaction.

"Spectral resolution" and "spectrally resolvable" in reference to a plurality of dyes means that the fluorescent emissions of the dyes are sufficiently distinct, i.e., sufficiently non-overlapping, that reagents to which the respective dyes are attached, e.g. polynucleotides, can be resolved on the basis of a fluorescent signal generated by the respective dyes using standard photodetection systems.

"Detection" refers to detecting, observing, or measuring a nucleobase oligomer on the basis of the properties of a covalently-attached detection label. Detection labels include, but are not limited to, fluorescent dyes, such as fluorescein and rhodamine derivatives, cyanine dyes, and energy-transfer dyes (Clegg, R., 1992; Cardullo, 1988).

"Primer" refers to an oligonucleotide capable of selectively annealing to a specified target nucleic acid and thereafter serving as a point of initiation of a primer extension reaction wherein the primer is extended in a 5'→3' direction.

"Primer extension reaction" refers to a reaction between a target/primer duplex and a nucleotide which results in the addition of the nucleotide to a 3'-end of the primer such that the added nucleotide is complementary to the corresponding nucleotide of the target nucleic acid.

The term "5'→3' nuclease activity" refers to an enzyme activity that cleaves nucleic acid at phosphodiester bonds. This activity can be either endo (cleaves at internal phosphodiester bonds) or exo (cleaves at the phosphodiester bond closest to either the 5' or 3' terminus of the nucleic acid strand.

The term "block" refers to a non-extendable oligonucleotide or nucleic acid analog complementary to the internal control polynucleotide. A block does not conduct polymerization or extension in the normal manner through extension of the 3' terminus of a DNA primer, with polymerase and deoxynucleotide 5'triphosphates. A block functions as a negative control element, essentially turning off amplification of the internal control polynucleotide and thereby precluding an increase in fluorescence derived from the internal control probe.

The term "self-quenching" refers to an intermolecular, energy transfer effect, e.g. a reporter and quencher are joined on an oligonucleotide in a configuration that permits energy transfer from the fluorophore to the quencher.

The term "end-point analysis" refers to a test where data collection occurs only when a reaction is complete. End-point analysis of the exonuclease assay entails reporter signal measurement when PCR is complete. Results are reported in terms of the change in fluorescence of the reporter signal, minus the internal control amplification fluorescence change.

The term "real-time analysis" refers to periodic monitoring during a test. Real-time analysis of the exonuclease assay measures reporter signal changes from cycle-to-cycle, minus the internal control amplification fluorescence change.

II. EXONUCLEASE ASSAY WITH INTERNAL CONTROL POLYNUCLEOTIDE AND BLOCK

The TaqMan® exonuclease assay (Holland etal, 1991; Lee etal; Livak, 1996) illustrated in FIG. 1 shows self-quenching probe 1, including both a reporter label, $F_1$, and a quencher label, Q, and target primers 3a and 3b hybridized to target polynucleotide 2. During the polymerization phase of amplification, the primers 3a and 3b are then extended using a polymerase enzyme thereby forming extended primers 4a and 4b, e.g., using a DNA polymerase. During the primer extension reaction, a 5'→3' nuclease activity of the polymerase serves to cut the probe 1 so as to form probe fragments, including reporter-bearing fragment 5 and quencher-bearing fragment 6. Thus, the reporter and quencher labels are separated thereby preventing energy transfer between the two and the emission of the reporter becomes unquenched upon digestion of the probe. An increase in fluoresence, detectable as $F_1$, results.

Figure 4:
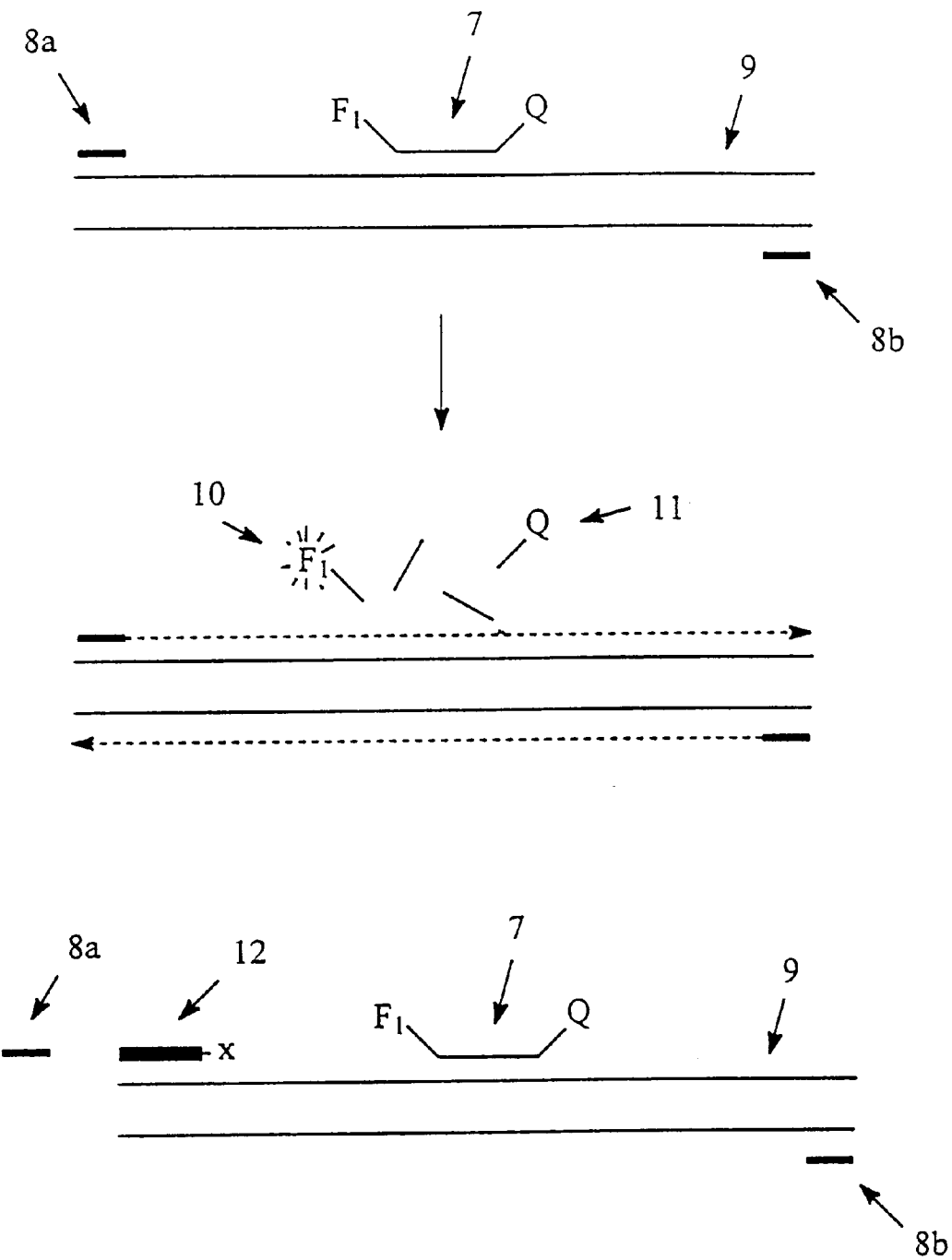
FIG. 4 Exonuclease assay of internal control polynucleotide; positive and negative control aspects FIG. 5 Chart of reporter and quencher spectral properties: emission and absorbance maxima FIG. 6 Self-quenching probe structure: 5' FAM reporter and 3' TAMRA quencher FIG. 7 Exonuclease assay results and sample assignment in 96-well format, with internal negative (A1–A6) and positive (A7–A-12) control wells.

When the internal control reagents and method of the present invention are practiced during the exonuclease assay, reagents additional to those above are added to the reaction chamber, including self-quenching probe 7 and primers 8a and 8b complementary to internal control polynucleotide 9 (FIG. 4). During the polymerization phase of amplification, the primers 8a and 8b are then extended using a polymerase enzyme thereby forming extended primers using a DNA polymerase. During the primer extension reaction, a 5'→3' nuclease activity of the polymerase serves to cut the probe 7 so as to form probe fragments, including reporter-bearing fragment 10 and quencher-bearing fragment 11. Thus, the reporter and quencher labels are separated thereby preventing energy transfer between the two and the emission of the reporter becomes unquenched upon digestion of the probe. An increase in fluorescence, detectable as $F_2$, results. Reporter dyes $F_1$ and $F_2$ are chosen to be spectrally resolvable. Quencher moieties on 1 and 7 may be the same or different.

When the negative internal control block 12 is added, no amplification of internal control polynucleotide 9 occurs. Non-extendable block 12 selectively binds to the 8a primer binding site, or at another site on 9, and precludes amplification. The self-quenching probe 7 remains intact and quenched. A negative control baseline may be measured and applied to positive control fluorescence changes.

III. DESIGN AND SYNTHESIS OF REAGENTS

Generally, the design and synthesis of oligonucleotides of the invention follows conventional teachings. Preferably, oligonucleotides are synthesized on an automated, solid-phase DNA synthesizer using phosphoramidite chemistry (Beaucage etal, 1992; Caruthers, 1983), e.g. Model 392 or 394 DNA synthesizer (PE Applied Biosystems, Foster City, Calif.).

a. Self-quenching probes

In designing self-quenching probes, the following general guidelines can be followed: (1) if the target nucleic acid sequence is located within a PCR amplicon, the probe sequence should be such that the probe hybridizes at a location on the sequence between the PCR primers; (2) probes should be about 20–30 nucleotides long so as to ensure good hybridization kinetics and specificity of binding; (3) avoid secondary structure in the probe and target nucleic acid sequence; (4) the probe should not hybridize to either of the forward and reverse primers; and (5) avoid probes with long stretches of a single nucleotide, i.e., more than four; and (6) when choosing between a probe sequence and its complement, pick the strand that has more C nucleotides than G nucleotides.

The self-quenching probe is designed so as to bring the reporter into close proximity with the quencher so as to permit efficient energy transfer from the reporter to the quencher. Guidance concerning the selection of an appropriate distance for a given embodiment is found in numerous references on resonant energy transfer between fluorescent reporter molecules and quenching molecules (also sometimes referred to as "donor" molecules and "acceptor" molecules, respectively), e.g. Clegg, 1992; Cardullo, 1988; Ozaki etal; Livak etal, 1995, and the like. Self-quenching probes may have intramolecular Watson/Crick base-pairing properties, i.e., self-complementarity. Adoption of a stable hydrogen-bonded conformation may result in a high-degree of energy transfer between the reporter and the quencher due to their enforced proximity (Tyagi etal, 1996; Tyagi etal, 1997). The increase in fluorescence of self-complementary, self-quenching probes ("Molecular Beacons") upon hybridization to target or internal control polynucleotides during amplification may be significant enough to not require exonuclease cleavage of the probes.

The reporter and quencher are preferably close enough so that substantially all, e.g. 90%, of the fluorescence from the reporter is quenched. Typically, for energy transfer-based quenching, the distance between the first and second fluorophores should be within the range of 10–100 angstroms. Preferably, the fluorescer and quencher are separated by between about 4 to 10 nucleotides. However, the invention includes embodiments in which the number of nucleotides separating the fluorophores may be greater than 10. Preferably, either the reporter and quencher are attached to the 5' terminal nucleotide of the oligonucleotide probe. The reporter and quencher may also be attached to the 3' terminal nucleotide. In other embodiments of the reference molecules of the invention, the fluorescer and quencher are attached at internal sites on the polynucleotide. The invention also includes embodiments in which one of the two fluorophores is located at an internal site and the other fluorophore is attached to a terminus of the polynucleotide.

Dyes employed as quenchers include fluorescent dyes whose fluorescent characteristics are substantially unaffected by the presence or association with nucleic acids, particularly double stranded DNA. A reporter-quencher pair for a particular probe is selected such that the emission spectrum of the reporter overlaps with the absorption of the quencher (FIG. 5). Spectral overlap allows for efficient energy transfer (FRET) when the probe is intact. Such dyes may include virtually any fluorescent dye fulfilling this criterion which is also spectrally resolvable from whatever fluorophores that are employed on reporter-quencher probes. Dyes suitable as reporters may also be suitable as quenchers. Similarly, dyes suitable as quenchers may also be suitable as reporters. In one embodiment of a self-quenching probe, 6-carboxyfluorescein (6-FAM) is used as the reporter and 6-carboxytetramethylrhodamine (TAMRA) is used as the quencher such that the TAMRA dye substantially quenches any fluorescent emissions by 6-FAM.

In addition to DNA and RNA oligonucleotides, various nucleic acid analogs may be employed as self-quenching probes, such as, (i) oxygens in the internucleotide linkage may be substituted by sulfur, carbon, or nitrogen, and (ii) the internucleotide phosphodiester linkages may be sulfate, carboxylate, amide, and the like. Alternatively, probes may have sugar modifications in one or more of the nucleosides, such as 2'-O-alkyl ribonucleosides and the like. Also, probes may have nucleobase modifications in one or more of the nucleosides, such as C-5-alkynyl pyrimidines and the like. The fluorophores may be joined to the oligonucleotide or nucleic acid analog by appropriate functionalization of the fluorophores and/or the polymer building blocks. Detailed description of how to join fluorophores to nucleic acids and analogs can be found liberally in the literature (Andrus, 1992; Andrus, 1995; Hermanson, 1996; Ju etal, 1995).

The reporters and quenchers of self-quenching probes can be covalently attached to predetermined nucleotides of an oligonucleotide by using nucleoside phosphoramidite monomers containing reactive groups. For example, such reactive groups can be on a phosphate, or phosphate analog (Agrawal, S. 1990), on the 5' hydroxyl when attachment is to the 5' terminal nucleotide (Andrus, 1995), and on base moieties (e.g. Ruth; Urdea etal; or the like). In further preference, the 3' terminal nucleotide of the oligonucleotide probe is blocked or rendered incapable of extension by a nucleic acid polymerase. Such 3' blocking is conveniently carried out by chemical attachment of a phosphate group (Horn, 1986; commercially available as PhosphaLink, PE Applied Biosystems). In a preferred embodiment of the invention, TAMRA is used as the quencher on self-quenching probes and the TAMRA dye is attached at the 3' terminus (Mullah, 1997; Mullah, 1998).

b. Block

The preferred block is a peptide-nucleic acid oligomer (PNA), a DNA analog in which the natural phosphodiester-deoxyribose backbone has been replaced by N-(2-aminoethyl)-glycine, a peptide-like unit (Nielsen, 1991). The nucleobases from natural nucleic acids, DNA and RNA, are retained through an amide linkage to the neutral backbone. The structure of PNA is represented below, where $B_1$ and $B_2$ are nucleobases.

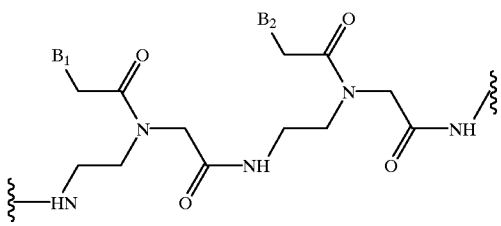

PNA oligomers are capable of recognizing complementary sequences by Watson/Crick base-pairing. Binding of PNA to its complement can occur in either a parallel or anti-parallel orientation of PNA; however, the anti-parallel duplex is much more stable (Egholm etal). The melting temperature of PNA/DNA and PNA/RNA hybrids are much higher than corresponding DNA/DNA or DNA/RNA duplexes due to a lack of electrostatic repulsion in the PNA containing duplexes. PNA oligomers can be synthesized by conventional methods on commercially available, automated synthesizers, e.g. the Model 394 (PE Applied Biosystems, Foster City, Calif.), with commercially available reagents (Vinayak, 1997; Van der Laan, 1997).

IV. KIT OF REAGENTS

An aliquot from a master mix of a kit comprised of an internal control polynucleotide, internal control primers, a non-extending oligonucleotide or nucleic acid analog complementary to the internal control polynucleotide, target primers, a polymerase having 5'→3' nuclease activity, self-quenching fluorescence probes, nucleotide 5'-triphosphates, and other reagents necessary for the exonuclease assay is delivered to all sample wells.

Embodiments of the invention include reagent compositions for use in nucleic acid amplification reactions. The subject compositions comprise a nucleic acid amplification buffer. The term "nucleic acid amplification buffer" as used herein, refers to a buffered aqueous solution that supports the enzymatic reaction or reactions required for a nucleic acid amplification reaction. The choice of buffer composition will vary in accordance with the particular enzyme selected for catalyzing the nucleic acid amplification reaction of interest (McPherson etal, 1991; McPherson etal, 1995; Dieffenbach, C., 1995). An example of a suitable nucleic acid amplification buffer for Taq DNA polymerase catalyzed amplification reactions is: 10 mM Tris (pH 8.4), 50 mM KCl, 1.5 mM $MgCl_2$, 0.01% gelatin, 0.01% NP40, and 0.01% Tween™.

The reagent compositions of the invention may be supplied in a concentrated form or in a form that does not require significant dilution prior to use. The reagent compositions may be used by adding additional compounds required for performing the assay of interest, such compounds include, a thermostable polymerase, nucleotides, target polynucleotide, a reporter-quencher probes, and the like. After the addition of the necessary additional compounds, the reaction mixture may then be processed accordingly, e.g., thermocycling, so as to produce the desired amplification results.

V. DETECTION OF PCR PRODUCTS

The real-time detection system includes optical components operationally associated with a closed reaction chamber, which comprises a lens for focusing an excitation beam into the reaction mixture and for collecting the resulting fluorescence and a fiber optic for transmitting both the excitation beam from a light source to the lens and the fluorescent signals from the lens to a detection and analysis means. To induce fluorescence during amplification, laser light can be distributed to 96 sample wells via a multiplexed array of optical fibers. The resulting fluorescent emission returns via the fibers and is directed to a spectrograph with a charge-coupled device (CCD) camera. Preferably, the reaction mixture is contained in a closed reaction chamber to prevent cross-sample contamination, or "carryover." The lens therefore focuses the excitation beam and collects fluorescence through a portion of a wall of the closed reaction chamber. The preferred reaction chamber is a tube, e.g. having the geometry and volume of a conventional microcentrifuge tube. The tube is closed after the reaction mixture is added by attaching a cap to the open end of the tube such that a leak-proof seal is formed. In a preferred embodiment of the sample interface for PCR, the lens directs the excitation beam and collects fluorescence generated by the probes through the cap of the tube. In other words, once a reaction mixture is placed in the tube and the cap is attached a closed reaction chamber is formed. Potential variability that could arise from sequential analysis of the first and second fluorescent signals is eliminated by simultaneously analyzing the signals by spectrally separating the signal light onto an array of photo detectors, e.g. by diffracting the signal onto a CCD array. An excitation beam generated by a single light source, e.g. a laser, is conveniently distributed to a plurality of closed reaction chambers by fiber optics. Likewise, the same fiber optics can collect the fluorescent signals from the plurality of reaction chambers for analysis by a single detection and analysis system. Alternatively the reaction chamber can be a well, e.g., a microtitre well, or a depression on a solid array. The array may be comprised of a plurality of spatially-addressable locations. Preferably, the system is employed with the PCR amplification of nucleic acids. An example of the preferred embodiment is the ABI PRISM™ 7700 Sequence Detection System (PE Applied Biosystems). Another embodiment is the ABI PRISM™ 7200 Sequence Detection System for end-point analysis. Preferably, the system of the invention is employed to monitor PCR, although it may also be employed with other amplification schemes.

VI. DATA ANALYSIS

The results of an exonuclease assay can be analyzed using two parameters; the Rn value and the Ct value. The Rn value is the ratio of the fluorescence of a reporter dye and the fluorescence of the passive reference at the end of a PCR experiment. The Rn is calculated for each of the target and the ICP:

Rn (target)=Emission intensity of target probe÷Emission intensity of passive reference Rn (ICP)=Emission intensity of ICP probe÷Emission intensity of passive reference The Ct value, or threshold cycle number, is the PCR cycle number at which the fluorescence ratio is distinguishable from the background. For a given reporter dye and a fixed concentration of target, both the Rn and Ct values reflect the efficiency of the quencher.

VII. EXAMPLES

The invention will be further clarified by a consideration of the following examples, which are intended to be purely exemplary of the present invention and not to in any way limit its scope.

EXAMPLE 1

Preparation of doubly-labeled, self-quenching probe for exonuclease assay

Figure 6:
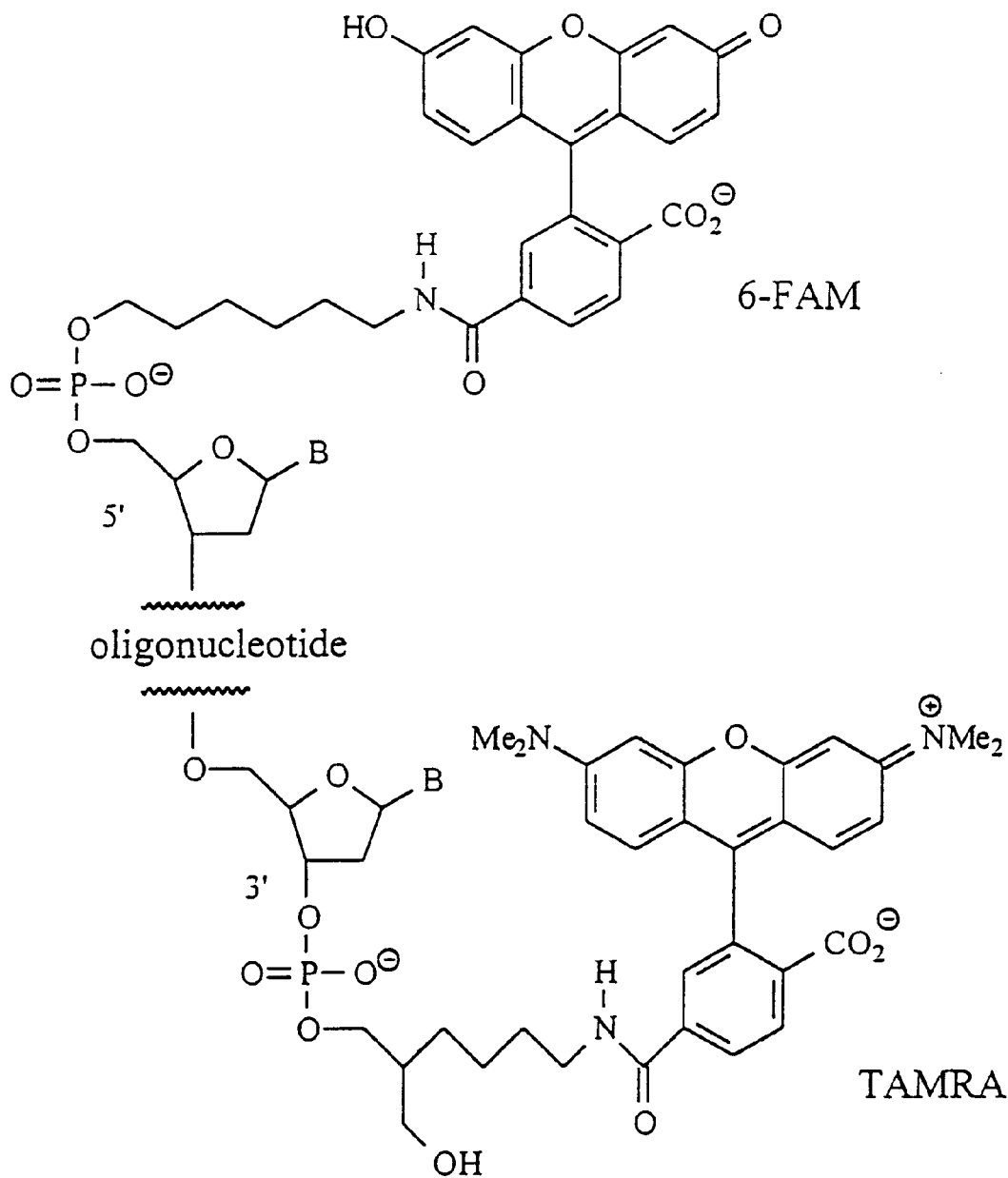

Automated synthesis of self-quenching probes can be performed using an Applied Biosystems Model 394 DNA/RNA synthesizer (The Perkin-Elmer Corporation, PE Applied Biosystems Division) according to the general procedures described in the users manual. A 5' FAM, 3' TAMRA probe can be synthesized at 0.2 μmol scale using TAMRA-labeled CPG solid supports (Mullah etal, 1997; Mullah etal, 1998), the set of phosphoramidite nucleosides $A^{bz}$, $G^{dmf}$, $C^{bz}$, T, other reagents recommended by the manufacturer (PE Applied Biosystems) and FAM dye-labeled phosphoramidite (Theisen etal). The standard 0.2 μmol synthesis cycle is slightly modified by extending coupling time of FAM amidite by an additional 120 seconds. Each probe includes a reporter dye attached to a 5'-end of and a quencher dye located at a 3'-end of the probe (FIG. 6).

After completion of the synthesis, oligonucleotides are autocleaved from the support on the DNA synthesizer by treating with a mixture of MeOH:t-BuNH$_2$:H$_2$O (1:1:2) (Woo, 1993) for a 1 hr autocleavage procedure as described in the operators manual for the Applied Biosystems Model 394 DNA/RNA synthesizer. Base protecting groups are removed by heating the mixture at 85° C. for 1 hr or at 65° C. for 3 h. The oligonucleotides can be analyzed and purified by reverse phase HPLC, anion-exchange HPLC, capillary gel electrophoresis, polyacrylamide gel electrophoresis, and other conventional techniques (Andrus, 1992).

EXAMPLE 2

Detection of C-myc mRNA by Exonuclease Assay using Exogenous IPC

Reverse-transcription

The cDNA is prepared using 50 ng human RNA and C-MYC reverse primer:

5'CAACATCGAT TTCTTCCTCA TCTTCT 3' (SEQ. ID NO. 1) in 100 μl solution containing 1× PCR buffer II, 5.5 mM MgCl$_2$, 500 μM each of dATP, dCTP, dTTP, and dGTP, 1.25 U/μl of MuLV reverse transcriptase, 0.4 U/μl RNase inhibitor, and RNase free H$_2$O at 48° C. for 30 min in an ABI Model 9600 thermal cycler.

Reagents

1) The following kit of reagents is mixed and 45 μl is dispensed into each of all 96 wells, A1–H12 (FIG. 7):
Tris-HCl pH 8.0, 100 mM, 16% glycerol, 0.1% gelatin, 0.02%, Tween 20™, 10 mM MgCl$_2$,
400 μM each of DATP, dCTP, deaza dGTP and 800 μM of dUTP,
0.1 U/μl of AmpliTaqGold DNA polymerase,
0.02 U/μl of Amperase UNG,
120 nM of Passive Reference,
forward C-MYC target primer:
  5'GCCCCTGGTT GCTCCATGA 3' (SEQ. ID NO. 2)
reverse C-MYC target primer
100 nM FAM labeled self-quenching target probe:
  5' -CAGCACAACT ACGCAGCGCC TCCT-TAMRA 3' (SEQ. ID NO. 3)
Exogenous Internal Positive Control (IPC) reagents:
  Plasmid DNA harboring a 80 bp amplicon internal control polynucleotide (IPC)
  50 nM forward IPC primer:
    5' TCCAACCGCC ACACTATCAA 3' (SEQ. ID NO. 4)
  50 nM reverse IPC primer:
    5' CATCCGCACA CTATCTCATC GT 3' (SEQ. ID NO. 5)
  200 nM of self-quenching IPC probe:
    5' JOE-CAGCTCGTTG ATCTTCCGTT CTGGCA-TAMRA 3' (SEQ. ID NO. 6)

2) Ten μl of the cDNA is added to each of 84 wells, B1–H12 (FIG. 7)

3) PNA block is added to wells A1–A6 (FIG. 7):
300 mM PNA block:
  H$_2$N -TCCAACCCGC CACCCACTAT C-CONH$_2$ (SEQ. ID NO. 7)

PCR

Human cDNA is amplified by thermal cycling conditions that begin with 2 min at 50° C., 10 min hold at 95° C. and then 40 cycles of: 15 sec denaturation at 95° C. and 1 min annealing and extension at 60° C. Thermal cycling and real-time fluorescence detection is conducted on an ABI PRISM™ 7700 Sequence Detection System (Perkin-Elmer Co.)

The target cDNA and IPC are amplified in the presence of the IPC, detected by the presence of FAM and JOE signals respectively in wells B1–H12. The PNA block inhibits the amplification of the IPC in wells A1–A6, detected by the absence of JOE signal. No target amplification is detected, by the lack of FAM signal, in wells A1–A12. IPC is amplified, as detected by JOE signal, in wells A7–A12 (FIG. 7).

EXAMPLE 3

Detection of DNA: NPTII gene from transgenic cotton plants by exonuclease assay with exogenous IPC Approximately 200 ng transgenic cotton genomic DNA is prepared by standard techniques for the 96 well test, Reagents The same kit of reagents as Example 2, including the same IPC reagents, is mixed and 45 μl total volume is dispensed into each of all 96 wells, A1–H12 (FIG. 7), including NPTII target specific primers and probe:

300 nM forward target primer:
  5' CAGGACGGGC GTTCCTTGC 3' (SEQ. ID NO. 8)
300 nM reverse target primer:
  5' GTGGGTCGAA TGGGCAGGTAG C 3' (SEQ. ID NO. 9)
200 nM self-quenching target probe:
  5' FAM -ACTGAAGCGG GAAGGGACTG GCT-TAMRA 3' (SEQ. ID NO. 10)

PCR

Amplification is conducted under the same conditions and on the same system as Example 2.

Both the cotton sample DNA and the IPC are successfully amplified. Comparison of the Ct with and without the IPC suggest that PCR efficiency is not affected by the complexity of the sample DNA.

EXAMPLE 4

Detection of E. Coli 0157:H7 by exonuclease assay with exogenous IPC

Approximately 100 ng. DNA from purified plasmid with cloned target sequence is prepared by standard techniques for the 96 well test. A range 10,000 to less than 1 copies per well are used in the unknown samples.

Reagents

The same kit of reagents as Example 2, including the same IPC reagents is mixed and 45 μl total volume is dispensed into each of all 96 wells, A1–H12 (FIG. 7), including NPTII target specific primers and probe:

300 nM forward target primer:
5' ATCCTGGACC AGGTTCCTGA 3' (SEQ. ID NO. 11)

300 nM forward target primer:
5' CGGTACAAGC TGCAACTGTTA 3' (SEQ. ID NO. 12)

200 nM Target probe:
5' FAM-TAGGCAGTAT TCCGAAATGAC-TAMRA 3' (SEQ. ID NO. 13)

PCR

Amplification is conducted under the same conditions and on the same system as Example 2.

The results are shown in FIG. 8. The unknown samples of 1 to 10,000 copies gave positive detection by detection of the FAM signal above background.

EXAMPLE 5

Detection of *Mycoplasma synoviae* DNA extracted from cultured cells by exonuclease assay with exogenous IPC Approximately 100 ng. DNA from multiple sources of *Mycoplasma synoviae* is prepared by standard techniques for the 96 well test. Each source is tested as ten-fold replicates.

Reagents

The same kit of reagents as Example 2, including the same IPC reagents is mixed and 45 μl total volume is dispensed into each of all 96 wells, A1–H12 (FIG. 7). The kit of reagents includes:

Forward Primer:
5' CGGATTGTAG TCTGCAACTCGACT A 3' (SEQ. ID NO. 14)

Reverse Primer:
5' ACAAACCGAC TTCGGGCATT 3' (SEQ. ID NO. 15)

Self-quenching probe:
5' FAM-AATACGTTCT CGGGTCTTGT ACACACCGC-TAMRA 3' (SEQ. ID NO. 16)

PCR

Amplification is conducted under the same conditions and on the same system as Example 2. The target amplicon length is 143 bp.

The results are shown in FIG. 9. All No Amplification Control samples (A1–A6), containing IPC, PNA block and no target, gave insignificant FAM or JOE signals, as expected. All No Template Control samples (A7–A12), containing IPC, no PNA block and no target, gave insignificant FAM and significant JOE signal, as expected. All Unknown samples (B11–H12), containing IPC, no PNA block, and target, gave true positive results, except for sample H8 (target Ct=40) indicating true negative.

All publications and patent applications are herein incorporated by reference to the same extent as if each individual publication or patent application was specifically and individually indicated to be incorporated by reference.

Although only a few embodiments have been described in detail above, those having ordinary skill in the molecular biology art will clearly understand that many modifications are possible in the preferred embodiment without departing from the teachings thereof. All such modifications are intended to be encompassed within the following claims.

We claim:

1. A method of conducting nucleic acid amplification control reactions in a single reaction chamber comprising:

providing an internal control polynucleotide, internal control primers, a non-extendable oligonucleotide or oligonucleotide analog complementary to the internal control polynucleotide, a target polynucleotide, target primers, a nucleic acid polymerase having 5'→3' nuclease activity, nucleotide 5'triphosphates; self-quenching fluorescence probes including reporter and quencher moieties, said probes existing in at least one single-stranded conformation when unhybridized wherein said quencher dye quenches the fluorescence of said reporter dye and at least one conformation when hybridized to said polynucleotides, wherein the fluorescence of the reporter dye is unquenched, the fluorescence intensity of reporter dye being greater than the fluorescence intensity of quencher dye when probe is hybridized to polynucleotide; and the steps of hybridizing said target primers to said target polynucleotide;

hybridizing said self-quenching fluorescence probes to the internal control polynucleotide and/or the target polynucleotide;

hybridizing said internal control primers to said internal control polynucleotide;

amplifying the target polynucleotide by PCR, whereby target polynucleotide amplification products are produced; and amplifying the internal control polynucleotide by PCR, whereby internal control polynucleotide amplification products are produced.

2. The method of claim 1 wherein said nucleic acid polymerase digests said probes during amplification to separate said reporter dye from said quencher dye.

3. The method of claim 1 wherein a first self-quenching fluorescence probe is complementary to the internal control polynucleotide and a second self-quenching fluorescence probe is complementary to the target polynucleotide.

4. The method of claim 3 wherein the reporter dye of the first self-quenching fluorescence probe is spectrally resolvable from the reporter dye of the second self-quenching fluorescence probe.

5. The method of claim 1 wherein a product of the nucleic acid amplification of the internal control polynucleotide is spectrally resolvable from the products of the nucleic acid amplification of the target polynucleotide.

6. The method of claim 1 wherein the products of the nucleic acid amplification of the internal control polynucleotide and target polynucleotide are measured and quantitated by end-point analysis.

7. The method of claim 1 wherein the products of nucleic acid amplification of the internal control polynucleotide and target polynucleotide are measured and quantitated by real-time analysis.

8. The method of claim 1 wherein the products of nucleic acid amplification of the internal control polynucleotide and target polynucleotide are measured by fluorescence detection.

9. The method of claim 1 wherein said nucleic acid polymerase is a thermal-stable polymerase with exonuclease activity.

10. The method of claim 1 wherein said reporter is a xanthene dye.

11. The method of claim 10 wherein said xanthene dye is a fluorescein dye.

12. The method of claim 11 wherein said fluorescein dye is selected from the group consisting of

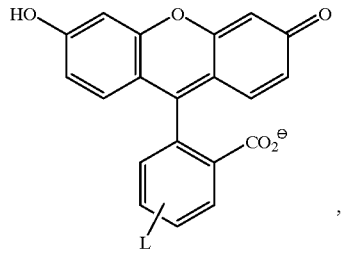

,

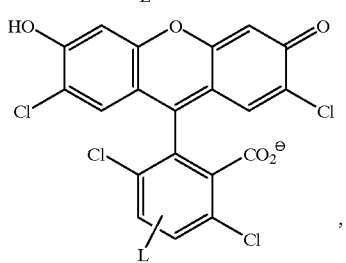

,

-continued

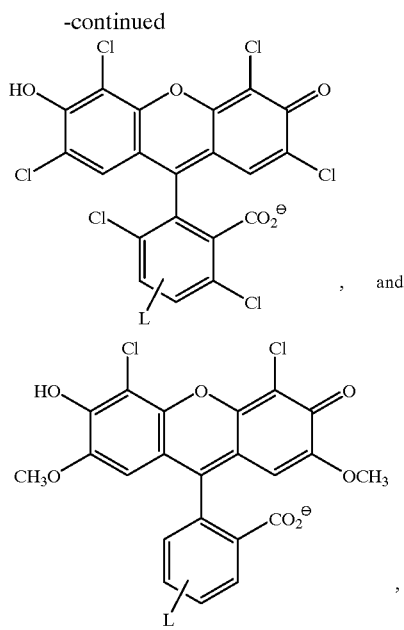

where L is a linker, and including substituted forms thereof.

13. The method of claim 1 wherein said quencher is selected from the group consisting of

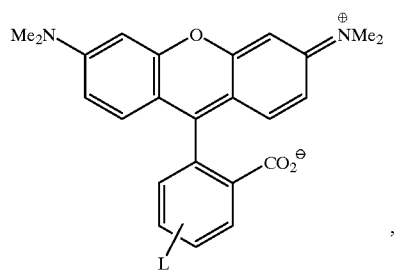

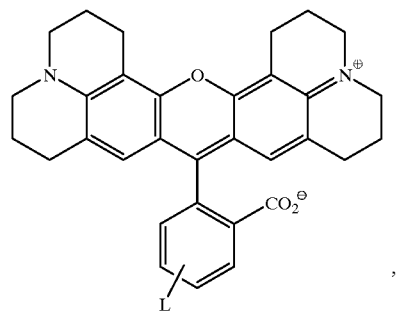

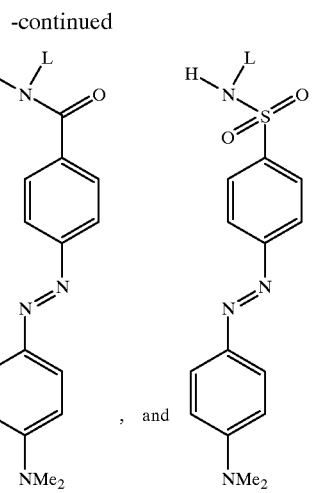

where L is a linker, and including substituted forms thereof.

14. The method of claim 1 wherein said reporter dye is separated from said quencher dye by at least 12 nucleotides.

15. The method of claim 1 wherein said reporter dye is attached at the 5' terminus or 3' terminus of the self-quenching fluorescence probe.

16. The method of claim 1 wherein said quencher dye is attached at the 5' terminus or 3' terminus of the self-quenching fluorescence probe.

17. The method of claim 1 wherein said non-extending oligonucleotide or nucleic acid analog complementary to the internal control polynucleotide is selected from the group consisting of

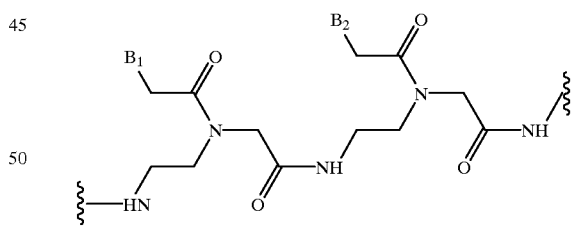

-continued

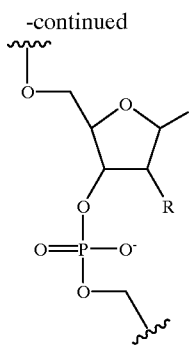

where R is fluoro, chloro, amino, —OCH$_3$, —OCH$_2$CH=CH$_2$, and —OCH$_2$CH$_2$OCH$_3$,

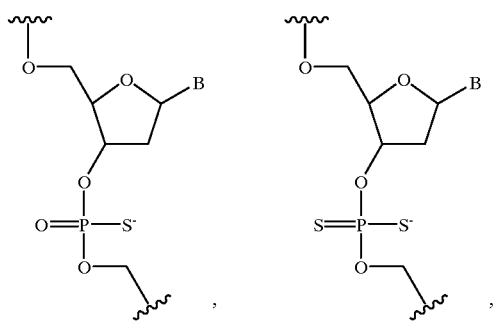

-continued

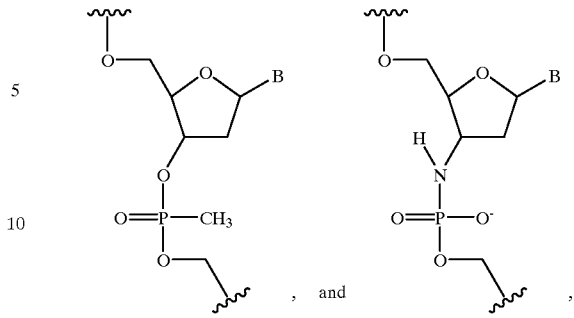

, and including substituted forms thereof.

18. A kit of reagents for nucleic acid amplification comprising:

an internal control polynucleotide, internal control primers, a non-extending oligonucleotide or nucleic acid analog complementary to the internal control polynucleotide, target primers, a nucleic acid polymerase having 5'→3' nuclease activity, self-quenching fluorescence probes including reporter and quencher moieties, nucleotide 5'-triphosphates; and other reagents necessary for nucleic acid amplification.

* * * * *

UNITED STATES PATENT AND TRADEMARK OFFICE
CERTIFICATE OF CORRECTION

PATENT NO.: 5,952,202

DATED: September 14, 1999

INVENTOR(S): Kazuko Aoyagi and Kenneth J. Livak

It is certified that error appears in the above-identified patent and that said Letters Patent are hereby corrected as shown below:

Face Page, [54] Title: Methods --For-- Using Exogenous, Internal Controls and Analogue Blocks During Nucleic Acid Amplification.

Signed and Sealed this

Third Day of April, 2001

Attest:

NICHOLAS P. GODICI

Attesting Officer

Acting Director of the United States Patent and Trademark Office